(12) United States Patent
Bereta et al.

(10) Patent No.: US 8,916,372 B2
(45) Date of Patent: Dec. 23, 2014

(54) **STRAIN OF *SALMONELLA ENTERICA* S. TYPHIMURIUM, ITS USE AND A METHOD TO OBTAIN A THERAPEUTIC VACCINE VECTOR**

(75) Inventors: Michal Bereta, Kraków (PL); Joanna Bereta, legal representative, Kraków (PL); Paulina Chorobik, Wieliczka (PL)

(73) Assignee: Jagiellonian University, Crakow (PL)

( * ) Notice: Subject to any disclaimer, the term of this patent is extended or adjusted under 35 U.S.C. 154(b) by 56 days.

(21) Appl. No.: 13/148,139

(22) PCT Filed: Feb. 23, 2010

(86) PCT No.: PCT/PL2010/050005
§ 371 (c)(1),
(2), (4) Date: Feb. 21, 2012

(87) PCT Pub. No.: WO2010/095966
PCT Pub. Date: Aug. 26, 2010

(65) Prior Publication Data
US 2012/0164687 A1    Jun. 28, 2012

(30) Foreign Application Priority Data
Feb. 23, 2009    (PL) .......................................... 387319

(51) Int. Cl.
| | | |
|---|---|---|
| C12P 21/00 | (2006.01) | |
| C12N 1/20 | (2006.01) | |
| A61K 39/112 | (2006.01) | |
| A61K 39/00 | (2006.01) | |
| A61K 38/00 | (2006.01) | |

(52) U.S. Cl.
CPC ....... *A61K 39/0275* (2013.01); *A61K 2039/523* (2013.01); *A61K 2039/522* (2013.01); *A61K 39/0011* (2013.01); *A61K 38/00* (2013.01)
USPC ..................... 435/252.3; 435/69.3; 435/252.8

(58) Field of Classification Search
None
See application file for complete search history.

(56) References Cited

PUBLICATIONS

Bereta et al. (Vaccine, vol. 25, pp. 4183-4192).*
Bereta et al. (Vaccine, vol. 25, pp. 4138-4192).*
Al-Ramadi et al., "Potent anti-tumor activity of systemically-administered IL2-expressing *Salmonella* correlates with decreased angiogenesis and enhanced tumor apoptosis," Clinical Immunology, 130(1):89-97 (2009).
Bereta et al., "Improving tumor targeting and therapeutic potential of *Salmonella* VNP20009 by displaying cell surface CEA-specific antibodies," Vaccine, 25:4183-4192 (2007).
Bermudes et al., "Live bacteria as anticancer agents and tumor-selective protein delivery vectors," Curr. Opin. Drug Discov. Devel., 5:194-199 (2002).
Burns et al., "Identification and sequence analysis of a silent gene (ushA0) in *Salmonella* typhimurium," J. Mol. Biol., 192:163-175 (1986).
Chatfield et al., "Evaluation of *Salmonella* typhimurium strains harbouring defined mutations in htrA and aroA in the murine salmonellosis model," Microb. Pathog., 12:145-151 (1992).
Cheminay et al., "Rational design of *Salmonella* recombinant vaccines," Int. J. Med. Microbiol., 298:87-98 (2008).
Clairmont et al., "Biodistribution and genetic stability of the novel antitumor agent VNP20009, a genetically modified strain of *Salmonella* typhimurium," J. Infect. Dis., 181:1996-2002 (2000).
Cossart et al., "Bacterial invasion: the paradigms of enteroinvasive pathogens," Science, 304:242-248 (2004).
Coynault et al., "Virulence and vaccine potential of *Salmonella* typhimurium mutants deficient in the expression of the RpoS (sigma S) regulon," Mol. Microbiol., 22:149-160 (1996).
Dougan et al., "Live oral *Salmonella* vaccines: potential use of attenuated strains as carriers of heterologous antigens to the immune system," Parasite Immunol., 9:151-160 (1987).
Dougan et al., Construction and characterization of vaccine strains of *Salmonella* harboring mutations in two different aro genes, J. Infect. Dis., 158:1329-1335 (1988).
Freeman et al., "The *Salmonella enterica* serovar typhimurium translocated effectors SseJ and SifB are targeted to the Salmonella-containing vacuole," Infect. Immun., 71:418-427 (2003).
Gentschev et al., "Vivotif-a 'magic shield' for protection against typhoid fever and delivery of heterologous antigens," Chemotherapy, 53:177-180 (2007).
Hersh et al., "The *Salmonella* invasin SipB induces macrophage apoptosis by binding to caspase-1," Proc. Natl. Acad. Sci. U S A, 96:2396-2401 (1999).
Hoiseth et al., "Aromatic-dependent *Salmonella* typhimurium are non-virulent and effective as live vaccines," Nature, 291:238-239 (1981).
Innes et al., "The cryptic ushA gene (ushA(c)) in natural isolates of *Salmonella enterica* (serotype Typhimurium) has been inactivated by a single missense mutation," Microbiology, 147:1887-1896 (2001).
King et al., "Tumor-targeted *Salmonella* expressing cytosine deaminase as an anticancer agent," Human Gene Therapy, 13:1225-1233 (2002).
King et al., "Tumour therapy using *Salmonella*," Emerging Drugs, 5(2):211-219 (2000).
Luo et al., "Antitumor effect of VNP20009, an attenuated *Salmonella*, in murine tumor models," Oncology Research, 12(11-12):501-508 (2001).
Papezova et al., "Ordered expression of virulence genes in *Salmonella enterica* serovar typhimurium," Folia Microbiologica, 52(2):107-114 (2007).
Pawelek et al., "Tumor-targeted *Salmonella* as a novel anticancer vector," Cancer Res., 57:4537-4544 (1997).

(Continued)

*Primary Examiner* — Robert A Zeman
(74) *Attorney, Agent, or Firm* — Fish & Richardson P.C.

(57) ABSTRACT

The present invention relates to a new bacterial strain of *Samonella* enterica serovar *Typhimurium* VNP20009 deposited in the Polish Collection of Microorganisms under access no. B/00024 and its us in the production of a vaccine, especially an anti-cancer vaccine. The present invention also relates to a method of obtaining a therapeutic vaccine vector, characterized in that a genetic modification is introduced into the vector strain specific to cancer cells, resulting in the delayed over expression of a gene encoding a protein responsible for the invasive ability of this strain.

5 Claims, 10 Drawing Sheets

(56) References Cited

PUBLICATIONS

Figure 1:
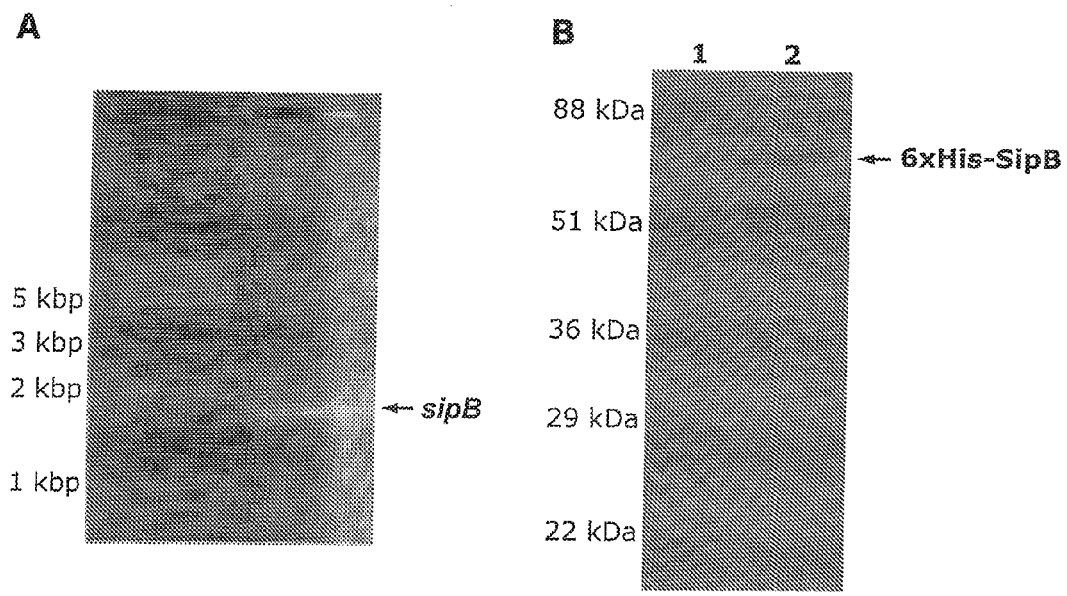

Posfai et al., "Markerless gene replacement in *Escherichia coli* stimulated by a double-strand break in the chromosome," Nucleic Acids Res., 27:4409-4415 (1999).

Sydenham et al., "*Salmonella enterica* serovar typhimurium surA mutants are attenuated and effective live oral vaccines," Infect. Immun., 68:1109-1115 (2000).

Toso et al., "Phase I study of the intravenous administration of attenuated *Salmonella* typhimurium to patients with metastatic melanoma," J. Clin. Oncol., 20:142-152 (2002).

International Search Report and the Written Opinion of the International Searching Authority for PCT/PL2010/050005, mailed Jul. 7, 2010.

International Preliminary Report on Patentability for PCT/PL2010/050005, issued Aug. 23, 2011.

\* cited by examiner

```
Primer D (sifF):
>ref|NC_003197.1| Salmonella typhimurium LT2, the whole genome
 gb|AE006468.1| Salmonella typhimurium LT2, the whole genome
length = 4857432
Query    4       AATGCCC-AGGATGCTGTCTTTTCGTGGATTTCACCATCTGATTTCTTCATTTTGAGCCT    62
                 ||||||| ||||||||||||||||||||| |||||||||||||||||||||||||||||
Sbjct    1691594 AATGCCCCAGGATGCTGTCTTTTCGTGAATTTCACCATCTGATTTCTTCATTTTGAGCCT    1691653
Query    63      CCTCGCAGGTTTTTATAATTTTATCGCCCAACTGGAAACAAAGCCGTCAGCTAATCGTTA    122
                 ||||||||||||||||||||||||||||||||||||||||||||||||||||||||||||
Sbjct    1691654 CCTCGCAGGTTTTTATAATTTTATCGCCCAACTGGAAACAAAGCCGTCAGCTAATCGTTA    1691713
Query    123     CAACAAATATAATTAAGACAAAAACTAAAGAGTAAGATATTTATATCATAAGCACTATCA    182
                 ||||||||||||||||||||||||||||||||||||||||||||||||||||||||||||
Sbjct    1691714 CAACAAATATAATTAAGACAAAAACTAAAGAGTAAGATATTTATATCATAAGCACTATCA    1691773
Query    183     GTATTGGCCTTCTGCCCTACCGCTAAACATCTCATTGTTGTTAGCCTAATAATACTTTTA    242
                 ||||||||||||||||||||||||||||||||||||||||||||||||||||||||||||
Sbjct    1691774 GTATTGGCCTTCTGCCCTACCGCTAAACATCTCATTGTTGTTAGCCTAATAATACTTTTA    1691833
Query    243     GTTTAACTTCTTATAAGACAATTTCTACACGGTTGAGCAACTATTTACTTTCTCTAAAAA    302
                 ||||||||||||||||||||||||||||||||||||||||||||||||||||||||||||
Sbjct    1691834 GTTTAACTTCTTATAAGACAATTTCTACACGGTTGAGCAACTATTTACTTTCTCTAAAAA    1691893
Query    303     TAATATAGTGCGTAATTAATCATTACTCATAGTACATGATGATGTGAGAATTAAGAAAAC    362
                 ||||||||||||||||||||||||||||||||||||||||||||||||||||||||||||
Sbjct    1691894 TAATATAGTGCGTAATTAATCATTACTCATAGTACATGATGATGTGAGAATTAAGAAAAC    1691953
Query    363     CGTTTTACTTTCATTCGTTTTATCTGACATATTTCATGGCCAGGAGGCGTGGGCATGACT    422
                 ||||||||||||||||||||||||||||||||||||||||||||||||||||||||||||
Sbjct    1691954 CGTTTTACTTTCATTCGTTTTATCTGACATATTTCATGGCCAGGAGGCGTGGGCATGACT    1692013
Query    423     AAAGCTACGGGTCGATTTGAACAATTGAACAATAATGTTGACGGTTCAGGACAAAGCAAA    482
                 ||||||||||||||||||||||||||||||||||||||||||||||||||||||||||||
Sbjct    1692014 AAAGCTACGGGTCGATTTGAACAATTGAACAATAATGTTGACGGTTCAGGACAAAGCAAA    1692073
Query    483     AATCAGGGGGTTTCCCCGATAGGCAAACCGATCGGGCCAACATGGGATAATATTTCCGAA    542
                 ||||| || ||||| |||||||||||||||||| |||||||||||||||| |||||
Sbjct    1692074 AATCA-GGTGTTTCACCGATAGGCAAACCGAT-GGGCAACATGGGATAATATTT-CGAAT    1692130
Query    543     ACCACCCTATTCCCAGGTAATGAA    566
                 |||| |||||||||  |||||||
Sbjct    1692131 ACCA-CCTATTCC--AGTAATGAA    1692151

Primer C (sipseq4):
>ref|NC_003197.1| Salmonella typhimurium LT2, the whole genome
 gb|AE006468.1| Salmonella typhimurium LT2, the whole genome
length = 4857432
Query    3       CCAGTAGGGTCTT--ACTTGCCA-GCAGTAATGTCAATTGCCCTTCGCTGGAGAGTTTTT    59
                 |||||||||| || | ||||||| |||||||||||||||||||||||||||||||||||
Sbjct    3030607 CCAGTAGGGTCATTAACTTGCCAAGCAGTAATGTCAATTGCCCTTCGCTGGAGAGTTTTT    3030666
Query    60      CCCGGGCGGCGTCCGTAGGCGGCTTTAGACCCACCGTATTAATAGCGCTCTCGCCGGACT    119
                 ||||||||||||||||||||||||||||||||||||||||||||||||||||||||||||
Sbjct    3030667 CCCGGGCGGCGTCCGTAGGCGGCTTTAGACCCACCGTATTAATAGCGCTCTCGCCGGACT    3030726
Query    120     TTGTTCCGGCTTTAAGGTCGCCCGCTTTCGTTGCCACCACATCTTTAAAAGCTTTATCCG    179
                 ||||||||||||||||||||||||||||||||||||||||||||||||||||||||||||
Sbjct    3030727 TTGTTCCGGCTTTAAGGTCGCCCGCTTTCGTTGCCACCACATCTTTAAAAGCTTTATCCG    3030786
Query    180     CCGCTTTTAAAAAGTCCGTGTTCTTACGAACGCCTTCAAAAGCCGCCTCAGCGAGGCGCC    239
                 ||||||||||||||||||||||||||||||||||||||||||||||||||||||||||||
Sbjct    3030787 CCGCTTTTAAAAAGTCCGTGTTCTTACGAACGCCTTCAAAAGCCGCCTCAGCGAGGCGCC    3030846
Query    240     GATTTTGGGTATATCCGCTACGGCTAATGCTACTT    274
                 |||||||||||||||||||||||||||||||||||
Sbjct    3030847 GATTTTGGGTATATCCGCTACGGCTAATGCTACTT    3030881
Query    340     ACTTCATTACTGGAAATAGGTGGTATTCGAA-TATTATCCCATGTTGCCCATCGGTTTGC    398
                 |||||||||||||||| |||||||||||||| ||||||||||||||||||||||||||||
Sbjct    1692153 ACTTCATTACTGGAA-TAGGTGGTATTCGAAATATTATCCCATGTTGCCCATCGGTTTGC    1692095
Query    399     CTATCGGTGAAACACCTGATTTTTGCTT-GTCCTGAACCGTCAACATTATTGTTCAATTG    457
                 |||||||||||||||||||||||||||| |||||||||||||||||||||||||||||||
Sbjct    1692094 CTATCGGTGAAACACCTGATTTTTGCTTGTCCTGAACCGTCAACATTATTGTTCAATTG    1692035
Query    458     TTCAATCCGACCCGTAGCTTTAGTCATGGccccccccTCCTGGGCCATGAAATATGTCCGA    517
                 ||||| ||||||||||||||||||||| ||        ||||||| ||||||||||||| |
```

Fig. 15B

```
Sbjct  1692034  TTCAAATCGACCCGTAGCTTTAGTCATGCCCACGCCTCCT-GGCCATGAAATATGTCAG-  1691977
Query  518     ATAAAACGAATGGAAGTAAAACGGGTTTTCTTAATTCCCCAATCCATCCGGGACCATTGA  577
               |||||||||||| ||||||||| |||||||||||||| | || |||| ||| | |||
Sbjct  1691976  ATAAAACGAATGAAAGTAAAAC-GGTTTTCTTAATTCTCACAT-CATCATGTACTA-TGA  1691920
Query  578     GTAAGGATTAA  588
               |||| ||||||
Sbjct  1691919  GTAATGATTAA  1691909
```

Primer E (FsipBgl):
>ref|NC_003197.1| Salmonella typhimurium LT2, the whole genome
 gb|AE006468.1| Salmonella typhimurium LT2, the whole genome
length = 4857432

```
Query  31      AAGTAGCATTAGCCGTCCCGGATATACCCAAAATCCGCGCCTCGCTGAGGCGGCTTTTGA  90
               ||||||||||||||||  |||||||||||||||||||||||||||||||||||||||||
Sbjct  3030881  AAGTAGCATTAGCCGTAGCGGATATACCCAAAATCCGCGCCTCGCTGAGGCGGCTTTTGA  3030822
Query  91      AGGCGTTCGTAAGAACACGGACTTTTTAAAAGCGGCGGATAAAGCTTTTAAAGATGTGGT  150
               ||||||||||||||||||||||||||||||||||||||||||||||||||||||||||||
Sbjct  3030821  AGGCGTTCGTAAGAACACGGACTTTTTAAAAGCGGCGGATAAAGCTTTTAAAGATGTGGT  3030762
Query  151     GGCAACGAAAGCGGGCGACCTTAAAGCCGGAACAAAGTCCGGCGAGAGCGCTATTAATAC  210
               ||||||||||||||||||||||||||||||||||||||||||||||||||||||||||||
Sbjct  3030761  GGCAACGAAAGCGGGCGACCTTAAAGCCGGAACAAAGTCCGGCGAGAGCGCTATTAATAC  3030702
Query  211     GGTGGGTCTAAAGCCGCCTACGGACGCCGCCGGGAAAAACTCTCCAGCGAAGGCAATT  270
               ||||||||||||||||||||||||||||||||||||||||||||||||||||||||||||
Sbjct  3030701  GGTGGGTCTAAAGCCGCCTACGGACGCCGCCGGGAAAAACTCTCCAGCGAAGGCAATT  3030642
Query  271     GACATTACTGCTTGGCAAGTTAATGACCCTACTGGGCGATGTTTCGCTGTCTCAACTGGA  330
               ||||||||||||||||||||||||||||||||||||||||||||||||||||||||||||
Sbjct  3030641  GACATTACTGCTTGGCAAGTTAATGACCCTACTGGGCGATGTTTCGCTGTCTCAACTGGA  3030582
Query  331     GTCTCGTCTGGCGGTATGGCAGGCGATGATTGAGTCACAAAAAGAGATGGGGATTCAGGT  390
               ||||||||||||||||||||||||||||||||||||||||||||||||||||||||||||
Sbjct  3030581  GTCTCGTCTGGCGGTATGGCAGGCGATGATTGAGTCACAAAAAGAGATGGGGATTCAGGT  3030522
Query  391     ATGAAAGAATTCCAGACGGCTCTGGGAGAGGCTCAGGAGGCGACGGATCTCTATGAAGC  450
               | |||||||||||||||||||||||||||||||||||||||||||||||||||||||||
Sbjct  3030521  ATCGAAAGAATTCCAGACGGCTCTGGGAGAGGCTCAGGAGGCGACGGATCTCTATGAAGC  3030462
Query  451     CAGTATCAAAAAGACGGATACCGCCAAGAGTGTTTATGACGCTGCGACCaaaaaaaCTGA  510
               |||||||||||||||||||||||||||||||||||||||||||||||| |||||| |||
Sbjct  3030461  CAGTATCAAAAAGACGGATACCGCCAAGAGTGTTTATGACGCTGCGACC-AAAAAACTGA  3030403
Query  511     CGCAGGCGCAAAATAAATTGCAATCGCTGGGACCCGGGCTGACCCCGGCTATGCCCAAGC  570
               |||||||||||||||||||||||||||| |||||  ||||||| ||||||||| ||||||
Sbjct  3030402  CGCAGGCGCAAAATAAATTGCAATCGCT-GGACCC-GGCTGACCCCGGCTATGCACAAGC  3030345
Query  571     TGAAACCCACGGTAAAACCAGGGCCGGAAAAGAAACGACCAGAGCNCGAAAGAGGCCTTT  630
               || || || ||| |||   |||||||||||||| ||| ||| ||| |||||||||||||
Sbjct  3030344  TG-AAGCCGCGGTAGAAC--AGGCCGGAAAAGAAGCGA-CAGAGG-CGAAAGAGGCCTT-  3030291
Query  631     anaanaaGGNCCCNGGAAGGCNACCGGGTTAAAGCCAGGCNcnnaacccccaaangcnaa  690
                |||| |  | ||  ||||||| ||||| |||||||||| | ||||||| ||||| ||
Sbjct  3030290  -AGATAAGGCCACGG--ATGCGAC--GGTTAAAG-CAGGCACAGA--CGCCAAA-GCGAA  3030240
Query  691     angccnnanaaaGGCGGAATAACATT  716
               | ||| | ||| ||||  |||||||
Sbjct  3030239  A-GCC-GAGAAA-GCGG-ATAACATT  3030218
```

Primer A (Fushal):

Fig. 15C

```
>ref|NC_003197.1|  Salmonella typhimurium LT2, the whole genome
 gb|AE006468.1|  Salmonella typhimurium LT2, the whole genome
length = 4857432
Query    12      TGTGGGCCGTGCGGATTTCGAATTCCGTAACGGCGAGATG-AAATGGTT   59
                 ||||||||||||||||||||||||||||||||||||||||  ||||||||
Sbjct    554515  TGTGGGCCGTGCGGATTTCGAATTCCGTAACGGCGAGATGAAAATGGTT  554563
Query    138     TTTCTCCCTTTATTTTGGCAGTTTTTATGCGCGACTCTGGCGCAGAATAAAACGCGAAGC  197
                 ||||||||||||||||||||||||||||||||||||||||||||||||||||||||||||
Sbjct    3029090 TTTCTCCCTTTATTTTGGCAGTTTTTATGCGCGACTCTGGCGCAGAATAAAACGCGAAGC  3029149
Query    198     ATCCGCATTTTGCTGTACCGCAGAAGACATGGCTTTTTGCAGTTCCGCCGTTACCTTCTG  257
                 ||||||||||||||||||||||||||||||||||||||||||||||||||||||||||||
Sbjct    3029150 ATCCGCATTTTGCTGTACCGCAGAAGACATGGCTTTTTGCAGTTCCGCCGTTACCTTCTG  3029209
Query    258     GTTTTCACCAAATATTTCTACGGATTGTTTAAGCCACTGCTGAATCTGATCCATGGCAAA  317
                 ||||||||||||||||||||||||||||||||||||||||||||||||||||||||||||
Sbjct    3029210 GTTTTCACCAAATATTTCTACGGATTGTTTAAGCCACTGCTGAATCTGATCCATGGCAAA  3029269
Query    318     ACGGGCGAGCATAAAATCAGCAAGCGCCTCGCTGGCATTTTTAATAAATACGCCCCTCGG  377
                 |||||||||||||||||||||||||||||||||||||||||||||||||||| |||||||
Sbjct    3029270 ACGGGCGAGCATAAAATCAGCAAGCGCCTCGCTGGCATTTTTAATAAATACG-CCCTCGG  3029328
Query    378     CAACACCACCGGCTGACTGGGGCTGCGGTATTCGTGACTTCCATGCCCAACGCCACTTTA  437
                 ||||||||||||||||| ||||||||||||||||||||||||||||||||||||||||||
Sbjct    3029329 CAACACCACCGGCTGACT-GGGCTGCGGTATTCGTGACTTCCATGCCCAACGCCACTTTA  3029387
Query    438     TTTAGGGTATTACCTACCAGCTCTTTACTTAAGGCATTCGTTTGCAGGCCCATCTTGCTA  497
                 ||||||||||||||||||||||||||||||||||||||||||||||||||||||||||||
Sbjct    3029388 TTTAGGGTATTACCTACCAGCTCTTTACTTAAGGCATTCGTTTGCAGGCCCATCTTGCTA  3029447
Query    498     CCCACATTACCCAGACCGCTAGTAATACGTTGCATCCCCCTGGCGTAAAAAAGTTGGCTG  557
                 ||||||||||||||||||||||||||||||||||||  ||||||  |||  |||| ||||
Sbjct    3029448 CCCACATTACCCAGACCGCTAGTAATACGTTGCAT--CCCCTGGG--TAAAGAGTTTGCTG  3029504
Query    558     CCGTTTTGCGCCAACTGTTTCAGCCACGTTAGGCACCAAACTCCTTAATCCGTTTCGCCC  617
                 ||||||||||||||||||||||||  ||||||||||  ||||  ||||||  ||||||||
Sbjct    3029505 CCGTTTTGCGCCAACTGTTTCAG-CACGTTAGGCACC-AACTTCTTAAT-CGTTTCGCCC  3029561
Query    618     ATCAATTTTGGCTCAAGCNGGGTTACCCCAGTTT  651
                 ||||   |||  ||| |  |||||||||||||||
Sbjct    3029562 ATCA--TTTGCTC-AGC-GCGTTA-CCCAGTTT  3029590
```

Fig. 15D

A Fusha1 AATGGCATCTGGATCGTG
B sipseq3 GTAATCGCCTTGCCAATC
C sipseq4 AGACGAGACTCCAGTTGAGA
D sifF CCCAAGCTTGGGCCTTAGCCATTCTGACTG E FsipBgl GGAAGATCTTCCAGAGGAGAAATTAACTATGAGA
F sipseq1 GAGGCGACGGATCTCTAT
G sipseq2 CGCCTCACTATGCTCATG

STRAIN OF *SALMONELLA ENTERICA* S. TYPHIMURIUM, ITS USE AND A METHOD TO OBTAIN A THERAPEUTIC VACCINE VECTOR

CROSS REFERENCE TO RELATED APPLICATIONS

This application is a U.S. National Phase Application under 35 U.S.C. §371 of International Application PCT/PL2010/050005, filed on Feb. 23, 2010, which claims the benefit of Polish Application No. PL387319, filed on Feb. 23, 2009, the entire contents of which are hereby incorporated by reference in their entireties.

The present invention relates to the field of pharmacy, particularly the preparation of vaccines, especially of anti-cancer bacterial therapeutic vaccines. Bacteria belonging to the genus *Salmonella* are Gram-negative bacteria from the Enterobacteriaceae family which are disease-causing in humans and animals, and represent a serious medical and veterinary problem.

Vaccination with live, attenuated strains of *Salmonella* is an effective way to prevent the infection. Attenuated strains of *Salmonella* were obtained by introducing specific irreversible mutations into certain genes in the chromosome of *Salmonella*, such as: aroA (1), aroC (2), surA (3), htrA (4), rpoS (5), and galE (6).

Current methods of *Salmonella* attenuation which are used to obtain vaccine material are based on the introduction of genetically stable deletions that reduce or eliminate the virulence of bacteria, while they do not change or intensify their immunogenicity.

Through attenuation of wild strain *Salmonella typhi*, a new strain Ty21a was created and used for vaccination against typhoid fever. Attenuation of this strain has been achieved through a number of mutations induced by chemical mutagens. This has resulted in a strain that is sensitive to galactose (a mutation in galE gene), auxotrophic for isoleucine and valine (mutations in ilvD genes), has reduced resistance to stress (a mutation in rpoS), and is also unable to produce the Vi polysaccharide. The plurality of mutations makes the strain genetically stable and safe. Revertant mutations within the virulence genes were not observed either in vitro or in vivo (7, 8).

The strain CVD908 has clearly defined mutations in the genes aroC and aroD, but causes fever and other adverse reactions in volunteers vaccinated with high doses. Further attenuation of this strain by the deletion of htrA gene, which encodes a serine protease essential for bacterial survival in macrophages, led to strain CVD908-htrA, which is well tolerated even at high doses and shows high immunogenicity (9).

Mutants of *Salmonella* enterica serovar *Typhimurium*, lacking the transcription regulator RfaH effectively prevent salmonellosis when used to vaccinate mice. Lack of RfaH affects the expression of genes involved in the synthesis of lipopolysaccharide core and O-antigen. Such mutants do not differ in their ability to proliferate, but show increased susceptibility to antibacterial peptides (10).

Due to the specificity of preventive vaccines, aiming to elicit immune memory after administration, their activity may be based on the ability of attenuated bacteria to stimulate a humoral immune response (production of neutralising antibodies). The generation of an effective humoral response does not require the ability to invade host cells by *Samonella* sp. vaccines. This means that even relatively large deletions in the chromosome of *Salmonella* sp. may be tolerated in vaccinting material prepared for use as a preventive vaccine. However, the relative ease of attenuation does not always coincide with the retention of the original (effective) immunogenicity.

A therapeutic vaccine vector should be highly attenuated and possibly poorly immunogenic to provide effectiveness of repeated administration into a patient. In the case of conjugated heterogeneous (allo- or xenogenic) antigens (epitopes), the vector should demonstrate adjuvant properties (while maintaining its low immunogenicity). A therapeutic vector should be capable of stimulating a specific type of immune response, that is to induce a humoral (Th2) or cellular (Th1) response as needed.

The VNP20009 strain was developed as a vaccine vector whose task was to deliver non-toxic cytostatic drug precursors (prodrugs) to tumour tissue (9, 10). Deletions within the genes purI and msbB result in auxotrophism of the strain with a reduced capacity to stimulate TNF in the infected organism. Preliminary studies have shown the ability of preferential accumulation of VNP20009 within tumours in mice (11). VNP20009 was also found to have an inhibitory effect on tumour development. Phase I clinical studies have not confirmed the effects observed in small mammals. So far, there are no studies on the immunogenicity of VNP20009 in mice nor humans (12).

Surface expression of the variable fragment of a CEA-specific antibody (T84.66) improved the ability of selective accumulation of bacteria in malignant tumours (13). However, the stress caused by overexpression of the fusion protein OmpA-scFv (CEA-specific) substantially (100-fold) reduced the invasiveness of transformed VNP20009 (designated VNP/scFv). Despite the reduced invasiveness, an increase in therapeutic effects was observed for VNP/scFv versus VNP20009 in murine models of transplantable tumours stably transfected with the human CEA gene (MC38CEA and CT26CEA adenocarcinomas).

Another reason for the reduced effectiveness of VNP/scFv is probably genetic instability of the strain involving the loss of the plasmid (and hence the loss of ability to express OmpA-scFv) in the absence of antibiotic selection pressure. Reversion to wild type VNP20009 in the patient would not promote the targeting of the bacteria towards CEA-rich sites (tumour tissue).

In the case of a *Salmonella* sp., vector it is important to retain the invasive features of the bacteria, which are related to the quality of the immune mechanisms stimulated by those bacteria.

There is still a great need to develop expertise in the field of therapeutic vaccines. A particularly important issue is the impact of attenuation-related effects on the strength and type of immune response dependent on the type of microorganism.

The purpose of this invention is to provide an effective vaccine vector, particularly effective for the treatment of cancer.

The aim of the present invention is therefore to obtain the appropriate strain of *Salmonella* sp., pursuant to demand in the field of therapeutic vaccines as a vector for delivery of therapeutic material to target cells, particularly cancer cells, cells infected with a virus, etc., with immunogenicity resulting from the physiological intracellular location of bacteria. The subject of the present invention is a strain of *Salmonella* enlerica serovar *Typhimurium* VNP/sipB deposited in the Polish Collection of Microorganisms under access no. B/00024. Another subject of the present invention is the use of the strain of *Salmonella* enterica serovar *Typhimurium* VNP/ sipB deposited in the Polish Collection of Microorganisms under access no. B/00024 to produce a vaccine, especially anti-cancer vaccine.

Another subject of the present invention is a method of obtaining a therapeutic vaccine vector, characterized in that a genetic modification is introduced into the vector strain specific to cancer cells, resulting in a delayed overexpression of a gene encoding a protein responsible for the invasive features of this strain.

Preferably, this method of obtaining a therapeutic vaccine vector according to the present invention is characterized in that an expression cassette is obtained, containing a gene encoding a protein under the control of a promoter that controls its delayed overexpression, and then the cassette is integrated into the bacterial chromosome.

Preferably, the therapeutic vaccine vector according to the present invention is a bacterial strain of *Salmonella* genus, especially *Salmonella* enterica species, preferably a strain of *Salmonella* enterica serovar *Typhimurium* VNP20009.

Preferably, the gene encoding the protein is the sipB gene.

Preferably, the promoter controlling the delayed gene overexpression is the PsifB promoter.

Preferably, the expression cassette is integrated into the bacterial chromosome is the cassette PsifB-sipB according to SEQ ID 1 or the cassette ushA-5'-PsifB-sipB-ushA-3' according to SEQ ID 2.

In a preferred embodiment of the present invention, the method includes an additional final step of removing a gene for antibiotic resistance from the bacterial genome.

The subject of the present invention in an embodiment is made clear in the figure, in which:

FIG. 1A shows the electrophoretic separation of a PCR product in 1% agarose gel in the presence of ethidium bromide for the sipB gene sequence (1782 bp) obtained from the genomic DNA of a reference strain, *S. typhimurium* SL5319;

FIG. 1B shows the results obtained using Western blotting confirming the functionality of the cloned sipB gene;

FIG. 2 shows the results obtained as a result of the isolation of the sifB gene promoter and the results of functionality assays of the PsifB-GFP construct:

FIG. 2A shows the image of the electrophoretic separation of the PCR product in 1.2% agarose gel in the presence of ethidium bromide;

FIG. 2B shows a microscopic image of the RAW264.7 macrophage cell line infected with VNP20009 transformed with the pBR322-PsifB-GFP plasmid;

FIG. 2C shows the results of the cytofluorimetric analysis of bacterial cultures. VNP20009/PsifB-sipB-GFP: induction of the expression of the SipB-GFP fusion protein (right panel), GFP-negative bacteria (left panel);

FIG. 3 shows a diagram of the integration of the plasmid into the genome and DNA fragment exchange, stimulated by the cleavage of both DNA strands;

FIG. 4 shows the relative position of the sipB gene sequence, PsifB promoter and the insertion site of the PsifB-sipB cassette (ushA gene) in the genome of *Salmonella typhimurium* LT2;

FIG. 5 shows a diagram of the pSG76C plasmid including cloned cassette ushA-5'-PsifB-sipB-ushA-3';

FIG. 6 shows a diagram of the genomic sequence generated through the recombination of the ushA gene with a homologous region 5'-ushA of the plasmid. Primer sequences used for the analysis of chloramphenicol-resistant clones were indicated on the figure;

FIG. 7 shows the electrophoretic separation of RT-PCR products in 1% agarose gel in the presence of ethidium bromide: DNA of the mutated clone was amplified with the following primers: 1—A and B (2350 bp) 2—A and G (3755 bp) 3—A and F (4560 bp) 4—A and D, 5 —C and D (2411 bp); M—mass standard;

FIG. 8 shows the images obtained by electrophoretic separation of RT-PCR products in 1% agarose gel in the presence of ethidium bromide:

in FIG. 8A the image of the product of cDNA amplification with primers specific for PsifB-sipB (1222 bp): 1—VNP20009, 2—modified VNP20009, M—mass standard;

in FIG. 8B the image of the product of cDNA amplification with primers specific for sipB (389 bp; on the upper panel): 1—VNP20009, 2—modified VNP20009; product of cDNA amplification of 16S rRNA (350 bp; on the bottom panel); M—mass standard;

FIG. 9 shows the image of electrophoretic separation of the PCR product with primer sequences complementary to sequences flanking the ushA gene performed on the genomic DNA of a clone obtained through the procedure of PsifB-sipB integration into the VNP20009 chromosome; 1—amplification product with primers E and D (1526 bp), 2—product amplification with primer A and D (4709 bp), M—mass standard;

FIG. 10 shows a graph representing the results of the invasion of RAW264 cells by VNP20009 and VNP/sipB;

FIG. 11 shows the results of an experiment performed on lung metastasis model CT26CEA in Balb/c mice. The upper row shows the lungs of the control mice isolated on day 15 after the intravenous administration of $5\times10^5$ CT26CEA cells. White spots visible on the dark background are small tumour foci. The bottom row shows lungs explanted from mice, which were administered *Salmonella typhimurium* VNP/sipB bacteria intranasally in the amount of $2\times10^7$ CFU/mouse 48 hours after the injection of cancer cells;

FIG. 12 presents the result of an experiment performed on lung metastasis model CT26CEA in Balb/c mice. The upper row shows lungs of the control mice isolated on day 15 after intravenous administration of $5\times10^5$ CT26CEA cells. White spots visible on the dark background are small tumour foci. The bottom row shows lungs taken from mice, which were administered various modifications of *Salmonella typhimurium* intranasally in the amount of $2\times10^7$ CFU/mouse 96 hours after the injection of cancer cells; the mean numbers of tumour foci in the lungs are shown on the graph in the lower part of the figure.

FIG. 13 shows the results of an experiment performed on lung metastasis model B16F10 in C57Bl/6 mice. The upper row shows lungs of the control mice isolated on day 28 after intravenous administration of $5\times10^5$ B16F10 cells. Tumour sites are visible as dark spots. The middle and lower rows shows lungs isolated from mice, which were administered VNP (middle row) or VNP/sipB (bottom row) bacteria intranasally in the amount of $2\times10^7$ CFU/mouse 96 hours after the injection of cancer cells;

FIG. 14 shows the effect of antibody isotype skewing caused by selective stimulation of a Th1-type immune response by VNP/sipB. The results were produced by vaccination of Swiss mice (outbred) with VNP20009 strains: mice vaccinated with "wild type" VNP20009 (upper panel), mice vaccinated with VNP/sipB (lower panel);

FIG. 15 shows the result of DNA sequencing performed on a recombinant genomic DNA fragment of the modified strain of *Salmonella* enterica s. *Typhimurium* VNP20009:

FIG. 15A shows a DNA sequence, which includes sequences flanking ushA gene and complete sequence of the integrated PsifB-sipB construct that in VNP/sipB bacteria is located within the ushA gene.

FIG. 15B-15D present the results which confirm the identity of the sequence from VNP/sipB with template DNA from a model strain of *Salmonella typhimurium* LT2. Lower strand: template (lower strand of DNA), the location of the each element of the construct is indicated (sifB promoter, sipB ORF, ushA integration site) in accordance with the numbering of LT2 strain deposited in GenBank (NCBI) (SEQ ID NOS: 23, 25, 27, and 29). Upper strand: marked as "Query", shows the sequence obtained from the VNP/sipB (SEQ ID NOS: 22, 24, 26, and 28).

Figure 15:
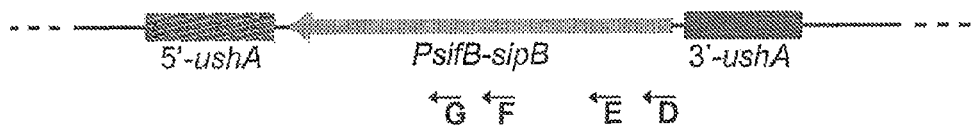
Figures 16, 17:
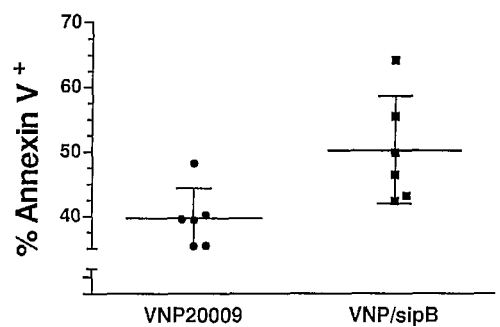

FIG. 16 shows the sequences of primers used in the sequencing of genomic DNA (top to bottom; SEQ ID NOS: 30, 31, 32, 5, 9, 33, and 16). A schematic location of the primers is indicated in FIG. 15 within the flanking sequences and the integrated construct.

FIG. 17 shows the Apoptosis of VNP20009- or VNP/sipB-infected MC38CEA cells, measured as a percentage of annexin V binding cells. Bacteria used for infection were expressing RFP. Annexin V-APC fluorescence was analyzed in RFP-positive population of MC38CEA cells.

Figure 10:
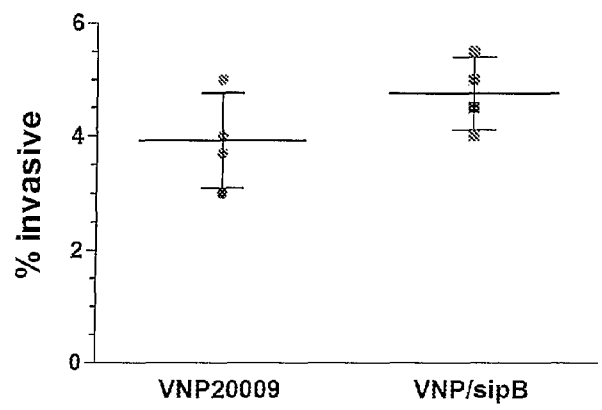

In the present invention the VNP/sipB vector was obtained with the full retention of invasive ability (FIG. 10).

The prepared vaccine vector utilised the natural ability of *Salmonella* sp. to infect host cells. The invasiveness of *Salmonella* sp. is a multifactorial process, which involves components of both the bacterial cells and the host cells (14). Adhesion of bacteria to a host cell causes the activation of Type III Secretion Systems genes (TTSS) grouped into the "*Salmonella* Pathogenicity Island-1" (SPI-1). Products of those genes, including the SipB protein, allow bacteria to penetrate the cell (15). Expression of another set of genes is activated inside the host cell. Those genes are located within the SPI-2 and their products facilitate the proliferation of the bacteria within the cytoplasm. The expression of SPI-2 genes is regulated by interaction of endoplasmatic factors with the SPI-2 promoters. The promoter of the sifB gene is one of those promoters (16).

Proliferation of the bacteria in the cytoplasm leads to apoptosis of the host cell, which in turn allows the bacteria to escape and subsequently infect other cells. One of the factors that induce apoptosis is the already mentioned SipB protein (14).

It was assumed that delayed (by using the promoter of sifB gene) overexpression of SipB (PsifB-sipB) will result in intracellular elimination of infective bacteria with simultaneous apoptosis/necrosis of the infected cells. Interim infection will form a strong signal for leukocyte migration to the infection site, but will not result in the infection of the population of newly-migrating immune cells.

The result produced by such a vaccine vector will be the eradication of tumours through the concerted action of the bacteria and the immune system.

The present invention is illustrated by the following embodiments:

EXAMPLE 1

Cloning of the SipB Gene

The sequence of the SipB gene (1782 bp) (FIG. 1A) was obtained from the genomic DNA of a reference strain *S. typhimurium* SL5319 using a PCR technique with the following primers:

```
                                                    (SEQ ID NO: 3)
5'  AACTGCAGAACCAATGCATTGGTTTCTCCCTTTATTTTGGCA (SEQ ID NO: 4)
3'  CGGGATCCCGAAGTAGCATTAGCCGTAGCG,
``` which contain restriction site PstII BamHI.

cDNA for sipB was cloned into the expression cassette of plasmid pQE30 to obtain a sequence encoding the fusion protein RGS-6His-SipB. The correctness of the sipB sequence was confirmed by sequencing of both strands of sipB cDNA.

The functionality of the cloned sipB gene was confirmed using a standard Western blot technique (FIG. 1B) performed on lysates of *E. coli* M15 incubated in the presence of IPTG (0.5 mM), using anti-His-tag antibodies.

The results of Western blot analysis showed that the expression of SipB with an inducible promoter was toxic to bacteria, as induced in the *E. coli* M15 strain (containing the plasmid pREP-4 with the lacI gene encoding the repressor protein). Protein expression was induced with 0.5 mM IPTG in *E. coli* M15 grown in TB medium at 25° C. up to an optical density of OD600≈1.0. Bacterial lysate was prepared from 120 ml of culture after a 2.5-hour induction and was purified on an IMAC chromatography resin, TALON BD. The collected fractions were separated with SDS-PAGE on 10% gel and the blots were probed with α-RGS-6His antibodies (Qiagen).

Molecular weight of the obtained product corresponded to the mass of SipB protein (62 kDa).

EXAMPLE 2

Isolation of SifB Gene Promoter And Construction of Sipb Gene Controlled by PsifB The coding sequence of the promoter region of sifB gene was obtained through PCR on genomic DNA of *Salmonella typhimurium* VNP20009, using the following primers: "forward" CCCAAGCTTGGGCCTTAGCCATTCTGACTG (SEQ ID NO: 5) with a HindIII restriction site and "reverse" GAAGATCTTCACTTCATTACTGGAATAGGTGGT (SEQ ID NO: 6) with a BglII restriction site. Concurrently, a sequence encoding GFP was obtained from the pGFPuv plasmid (Clontech) using PCR and the following primers: "forward" GAAGATCTTCTCACACAGGAAACAGCTATGAC (SEQ ID NO: 7) with a BglII restriction site and "reverse" GAAGATCTTCGCGCTCAGTTGGAATTCA (SEQ ID NO: 8), also with a BglII restriction site.

PCR products were cloned into the plasmid pGEM-TEasy (Promega) and propagated in *Escherichia coli* DH5α. Upon confirmation of sequence identity with a sequence obtained from GenBank database, the gfp gene was cloned into the BglII restriction site of the pGEM-TEasy-PsifB plasmid, which had been previously obtained from plasmid pGEM-TEasy-gfp. Intracellular induction of the PsifB promoter was confirmed in vitro by infection of the RAW264.7 macrophage cell line with VNP20009 bacteria containing the pGEM-TEasy-PsifB-gfp plasmid, with the gfp sequence cloned in forward or reverse orientation to the promoter. The sipB coding sequence with the RBS and 6His sequences was obtained from the pQE-sipB plasmid using PCR and the following primers:

"forward" GGA<u>AGATCTT</u>CCAGAGGAGAAATTAACTATGAGA, (SEQ ID NO: 9)

"reverse" GA<u>AGATCTT</u>CGGAGTCCAAGCTCAGCTA (SEQ ID NO: 10)

(both primers with a BglII restriction site).

The PCR product was cloned into the pGEM-TEasy-PsifB plasmid into the BglII site. PsifB-sipB cassette was excised from pGEM-TEasy-PsifB-sipB plasmid with the restrictase NotI and after filling the sticky ends, it was cloned into a low-copy pBR322 plasmid (in EcoRV-NruI cloning site) and into pMoPac2-lpp-ompA-scFv plasmid.

Figure 2:
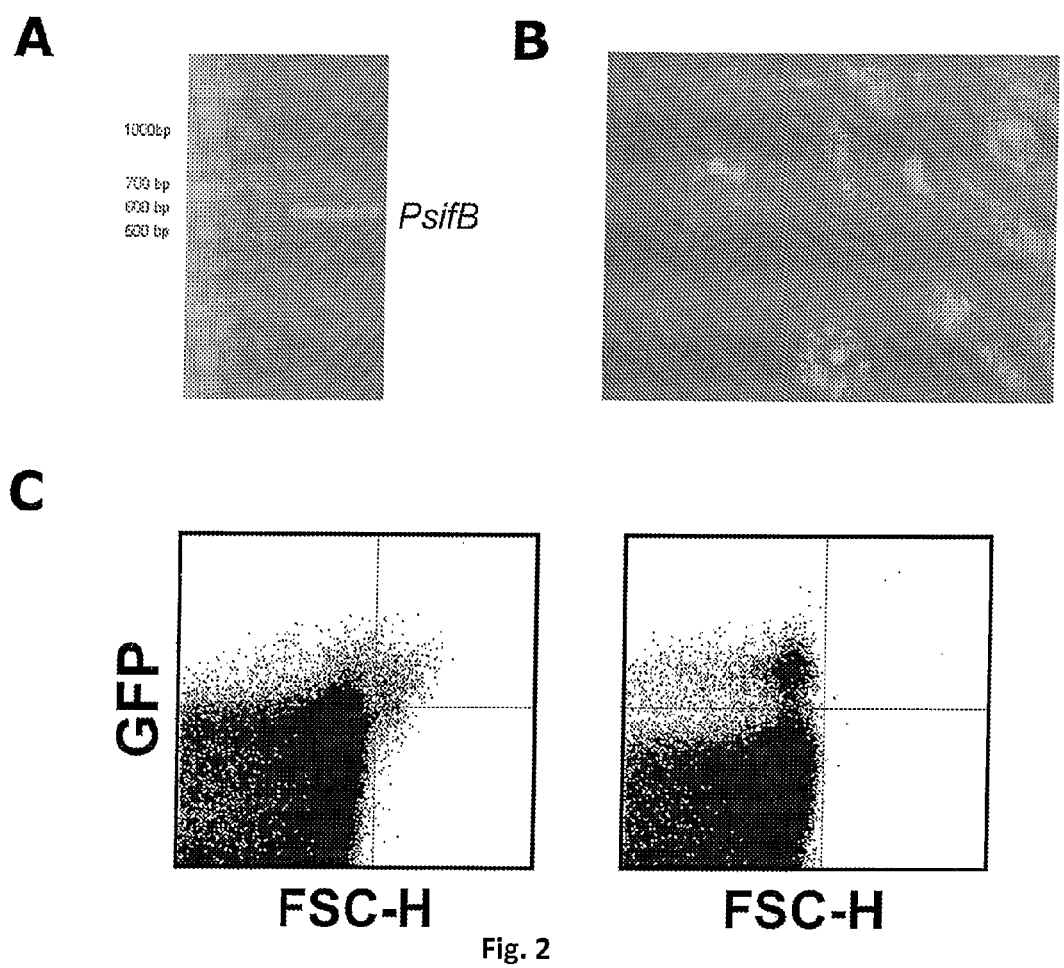

FIG. 2 presents the results of sifB gene promoter isolation and functional tests of PsifB-GFP construct.

FIG. 2A shows an electrophoretic image of PCR product separation in 1.2% agarose gel in the presence of ethidium bromide. The coding sequence of the promoter region of sifB gene (603 bp) was obtained using PCR from the genomic DNA of *Salmonella typhimurium*. The identity of the sequence was confirmed with the sequence obtained from GenBank (*Salmonella typhimurium* LT2, 1 691 572-1 692 152 bp). To confirm the functionality of the obtained promoter sequence, a transcriptional fusion protein PsifB-GFP was produced (gfp sequence amplified from the pGFPuv plasmid (Clontech) using PCR). Concurrently, the RBS-RGS-6His-sipB sequence was obtained from plasmid pQE30-sipB via PCR.

FIG. 2B shows a microscopic image obtained of the RAW264.7 macrophage cell line infected with VNP20009 transformed with the pBR322-PsifB-gfp plasmid. Induction of the PsifB promoter in intracellular bacteria was evaluated microscopically. VNP20009 transformed with low-copy plasmid (pBR322) or high-copy plasmid (pGEM-TEasy), both including the PsifB-gfp cassette, did not demonstrate any microscopically detectable GFP expression when grown in TB medium.

FIG. 2C presents the results of cytofluorimetric analysis performed on the bacterial culture. VNP20009/PsifB-sipB-gfp (but not *E. coli* DH5α/PsifB-sipB-gfp), cultured for 12 hours at 30° C. with shaking (180 RPM) in eukaryotic cell culture medium OPTI-MEM® (reduced serum medium) (Invitrogen), showed the induced expression of the fusion protein SipB-GFP (right panel). The same bacteria cultured in TB were GFP-negative (left panel).

The use of plasmid constructs is limited in vivo due to the frequent loss of plasmids from bacteria in the absence of selection pressure (antibiotics). Yet genetic stability is one of the fundamental features of bacteria that allows their use as vaccine material. A method of obtaining genetically stable bacterial strains is the integration of functional cassettes (promoter-gene) into the bacterial chromosome.

EXAMPLE 3

Integration of the PsifB-SipB Expression Cassette into the VNP20009 Chromosome

Figure 3:
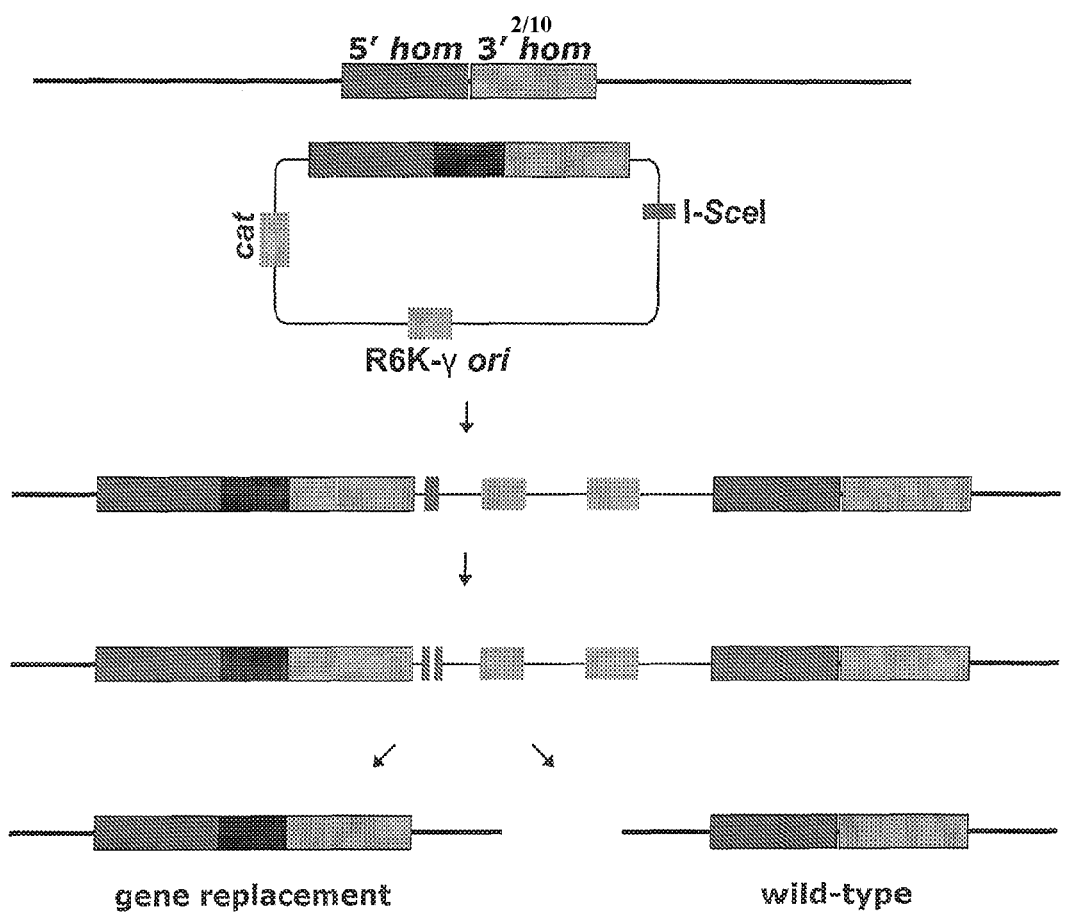

In order to obtain a genetically stable, attenuated strain of *Salmonella typhimurium* with the overexpression of endogenous SipB protein induced inside an infected cell, the PsifB-sipB expression cassette was integrated into VNP20009 genome. Integration was performed by the homologous recombination method, based on the natural recombination and repair system of the bacteria (Rec-A protein activity) and using a conditionally replicating plasmid as a vector for delivering a mutant allele into genomic DNA (17). At a temperature not permitting multiplication of the plasmid, clones which integrated the plasmid (as a result of recombination with wild and mutant copies of the gene) and acquired chromosomal resistance are selected in the presence of an antibiotic. At this stage, homologous regions of the modified gene are duplicated in the genome. In the next stage, an exchange occurs between the duplicated sequences, stimulated by cleavage of DNA sequences within the plasmid sequence present in the genome. The result is a return to the wild allele form or replacement into the mutated form, with simultaneous excision of the antibiotic resistance gene. A diagram of gene exchange by recombination of homologous segments stimulated by DNA cleavage is shown in FIG. 3.

The region of the ushA gene (STM0494) was chosen as the target site for integration, as it has a high homology with the ushA gene of *Escherichia coli*, but very low expression and low activity of the encoded enzyme in *Salmonella typhimurium* (UDP-glucose hydrolase with a point mutation, "silent gene"). The ushA gene has been inactivated in strains of *S. typhimurium* and its active functional homologue is ushB. The DNA sequences of these genes do not show a significant homology (18, 19). Considerable distance between ushA and sequences PsifB and sipB in *S. typhimurium* genome (FIG. 4) should reduce the genomic instability of the modified strain, associated with the introduction of additional copies of those sequences, which may be a substrate for homologous recombination.

Figure 4:
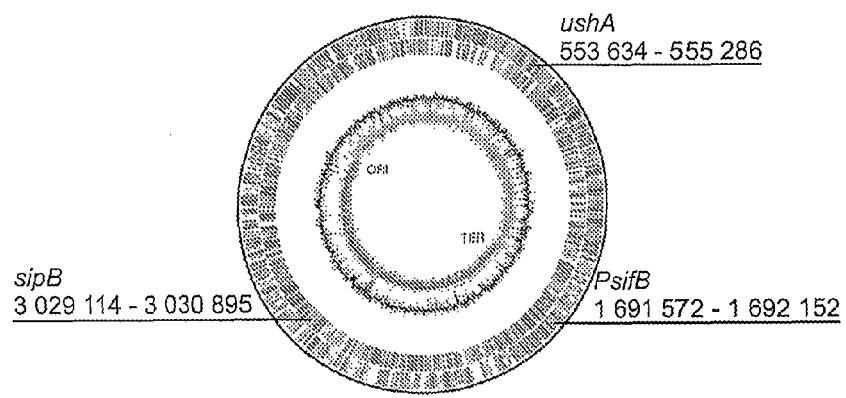

A conditionally replicating plasmid, pSG76-C, was used for the integration. The PsifB-sipB sequence was cloned into the plasmid, flanked with regions of homology, i.e. segments of sequence identical to the target sequence of integration within the bacterial chromosome (5'-ushA and 3'-ushA); chloramphenicol resistance gene for selection of clones, in which crossing-over occurred; ori R6Kγ and an extremely rare restriction site for endonuclease I-SceI (FIG. 4).

Replication of the pSG76-C plasmid requires protein II, supplied with an auxiliary plasmid pPIR-A (with thermosensitive ori pSC101). Plasmid pSG76C-ushA-PsifB-sipB can be built into the genome by a single crossing-over involving a region of homology and the corresponding chromosomal region. At a temperature preventing the replication of the plasmid pPIR-A (37-42° C.), and thus also plasmid pSG76C, in the presence of the antibiotic, there is a selection of clones with the plasmid sequence integrated into the genome. At this stage, flanking regions of homology are duplicated in the genome. Then, expression of I-SceI meganuclease is induced from the pSTKST auxiliary plasmid. The cleavage of both DNA strands within the integrated plasmid sequence stimulates the Rec-A-dependent intramolecular recombination (double strand break-stimulated gene replacement)—a repair of the DNA break occurs, with the use of adjacent flanking regions of homology. Single crossing-over could happen with the participation of the regions of 5'-ushA or 3'-ushA. In the first case the region of integration returns to the wild form (restoration of the ushA gene sequence integrity); in the second case, a productive re-arrangement occurs, with simultaneous removal of the antibiotic resistance gene. A modified bacterial strain is obtained as a result, without any selection marker in the form of antibiotic resistance gene or any other exogenous sequence.

EXAMPLE 4

Cloning the ushA-5'-PsifB-sipB-ushA-3' Cassette into the pSG76-C Plasmid

Complementary DNA for ushA was obtained from the genomic DNA of VNP20009 using PCR and the following primers:

```
forward FushA GGGGTACCCCGCGATGTTGGAGATAGTAGG,
                                          (SEQ ID NO: 11)

reverse RushA GGGGTACCCCTACAGCCAGCTCACCTCA,
                                          (SEQ ID NO: 12)
``` both containing a restriction site for the enzyme KpnI. The PCR product (1825 bp) was cloned into the pGEM-TEasy plasmid (Promega) and propagated in *Escherichia coli* DH5α. Upon confirmation of sequence identity with a sequence obtained from the GenBank database, the PsifB-sipB sequence (obtained from pGEM-TEasy-PsifB-sipB) was cloned into the restriction site HpaI, located within ushA. The orientation of the PsifB-sipB sequence was the reverse of the orientation of the ushA gene.

Figure 5:
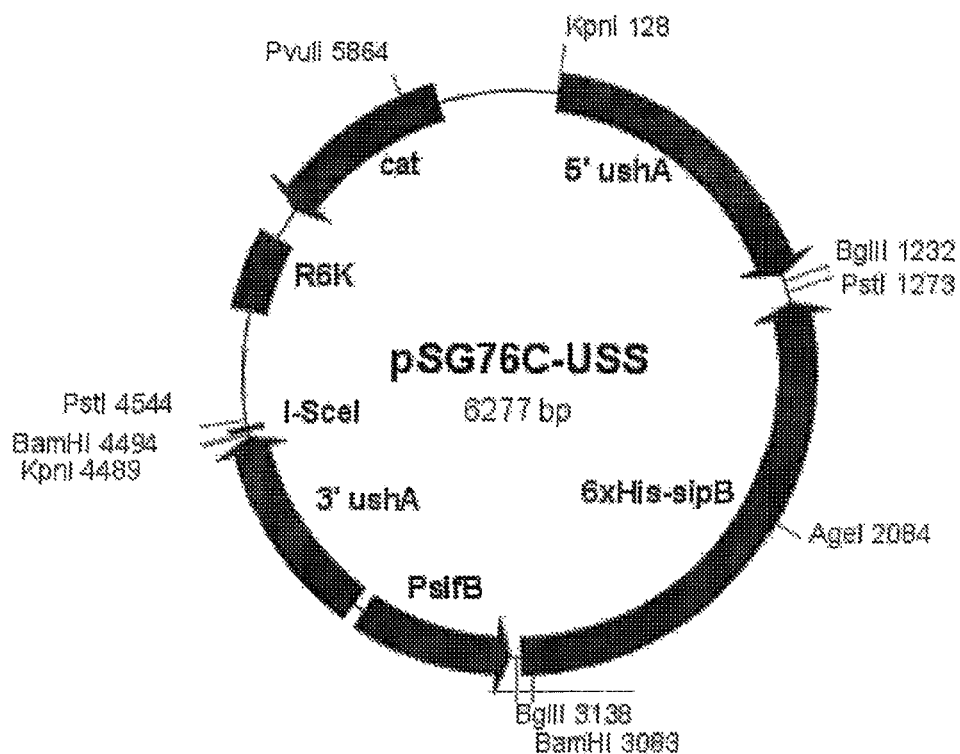

In the thusly obtained construct, the PsifB-sipB sequence is flanked with a 1091 by fragment of ushA at 5'-end and a 732 by fragment at 3'-end. Then, the ushA-5'-PsifBsipB-ushA-3' cassette was cut out with KpnI enzyme and cloned into pSG76-C in KpnI site, yielding pSG76C-USS (FIG. 5).

EXAMPLE 5

Integration of the pSG76C-USS Plasmid into VNP20009 Chromosome

The plasmid was amplified in *Escherichia coli* DH5α.pir (with the genomic copy of pir gene, encoding II protein) and transformed into the VNP20009 strain (by electroporation), which had been previously transformed with the pPIR-A plasmid. Then, the VNP20009 bacteria were cultured on solid medium as follows: 40 hours at 30° C. with ampicillin and chloramphenicol, 5 hours at 30° C. with chloramphenicol, 17 hours at 42° C. with chloramphenicol and 7 hours at 37° C. with chloramphenicol, for the selection of clones that have acquired the chromosomal antibiotic resistance. Among the transformants resistant to chloramphenicol, 5 large colonies of bacteria were selected, transferred to solid medium with chloramphenicol and cultured for additional 20 hours at 37° C. Then the selected clones were tested for integration of the plasmid into chromosome, that is, whether the plasmid was inserted into the ushA gene. PCR was carried out with a pair of primers complimentary to sequences flanking the insertion site and to the plasmid sequence and PsifB-sipB (FIG. 5, Table 1), with the following conditions: 94° C. 90 sec, 94° C. 45 s, 58° C. 30 s, 72° C. for 2 min 30 sec, 28 cycles.

Figure 6:
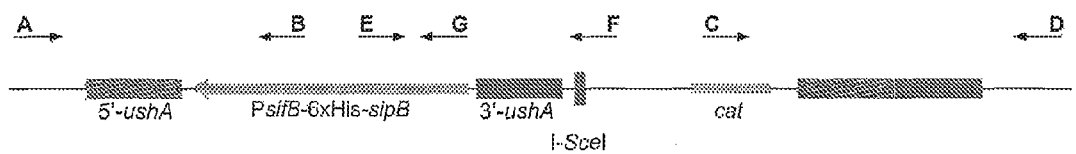

Accordingly, a diagram of genomic sequence generated by recombination between ushA gene and homology region 5'-ushA of the plasmid in shown FIG. 6. The position of the primers used for the analysis of chloramphenicol-resistant clones is also indicated.

The primers used in the experiment are listed in Table 1:

TABLE 1

Primer sequences used for analysis of recombinant clones and mass of PCR products confirming the integration of the plasmid into the genome within the ushA gene sequence.

| PRIMER | SEQUENCE (5'-3') | PRODUCT-WILD TYPE | PRODUCT AFTER INTEGRATION |
|---|---|---|---|
| FushA | GGGGTACCCCGCGATGTTGGAGATAGTAGG (SEQ ID NO: 13) | 1825 bp | 8366 bp |
| RushA | GGGGTACCCCTACAGCCAGCTCACCTCA (SEQ ID NO: 14) | | 4366 bp (after removal of resistance gene) |
| A | GCGACTGGATCATATCGT (SEQ ID NO: 15) | — | 2350 bp |
| B | CGCCTCACTATGCTCATG (SEQ ID NO: 16) | | |
| C | CTGAACGGTCTGGTTATAGG (SEQ ID NO: 17) | — | 2411 bp |
| D | CTGGATATTGAACTGGCG (SEQ ID NO: 18) | | - (after removal of resistance gene) |
| A | GCGACTGGATCATATCGT (SEQ ID NO: 15) | 2168 bp | 8709 bp |
| D | CTGGATATTGAACTGGCG (SEQ ID NO: 18) | | 4709 bp (after removal of resistance gene) |
| E | CCCAAGCTTGGGCCTTAGCCATTCTGACTG- (SEQ ID NO: 19) | | 5140 bp |
| D | CTGGATATTGAACTGGCG (SEQ ID NO: 18) | | 1526 bp (after removal of resistance gene) |
| A | GCGACTGGATCATATCGT (SEQ ID NO: 15) | — | 4560 bp |
| F | GCAGGTCGACTCTAGAGGAT (SEQ ID NO: 20) | | - (after removal of resistance gene) |
| A | GCGACTGGATCATATCGT (SEQ ID NO: 15) | — | 3755 bp |

TABLE 1-continued

Primer sequences used for analysis of recombinant clones and mass of PCR products confirming the integration of the plasmid into the genome within the ushA gene sequence.

| PRIMER | SEQUENCE (5'-3') | PRODUCT-WILD TYPE | PRODUCT AFTER INTEGRATION |
|---|---|---|---|
| G | CCCAAGCTTGGGCCTTAGCCATTCTGACTG (SEQ ID NO: 21) | | |

Figure 7:
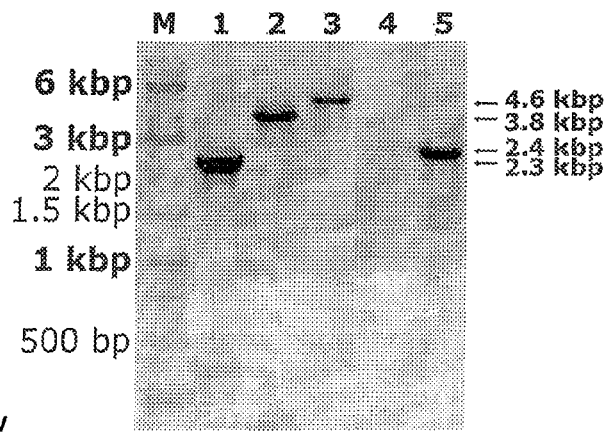

In the case of plasmid integration into ushA gene in PCR with primers A and B, a product of 2350 by was obtained and with primers C and D—a 2411 by product, while the standard PCR with primers A and D did not yield any product (FIG. 7).

FIG. 7 shows an electrophoretic image of the separation of PCR in a 1% agarose gel in the presence of ethidium bromide. DNA of the mutated clone was amplified using the following primers: 1—A and B (2350 bp) 2—A and G (3755 bp) 3—A and F (4560 bp) 4—A and D, 5—C and D (2411 bp).

Total RNA was isolated from wild-type VNP20009 bacteria and a clone positive for the integration, cultured in conditions that induced the PsifB promoter activity. In a RT-PCR with primer specific for the sipB copy newly introduced into the genome (complementary to the sequence including the synthetic RBS sequence) performed on a template derived from the mutant clone, a product was obtained with molecular mass corresponding to 1222 by (FIG. 8).

Figure 8:
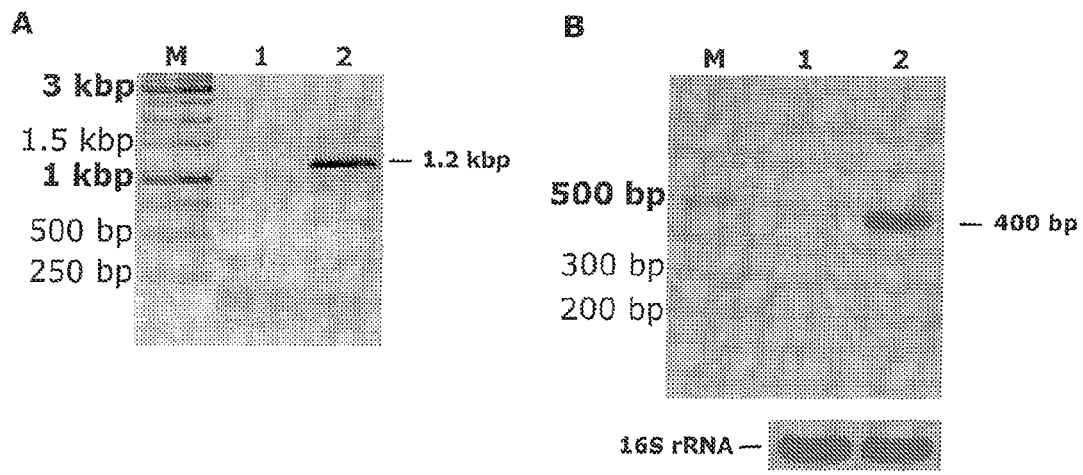

FIG. 8 shows the images obtained by electrophoretic separation of RT-PCR products in 1% agarose gel in the presence of ethidium bromide. RNA was isolated from bacteria cultured under PsifB promoter-inducing conditions. (A) Product of cDNA amplification with primers specific for PsifB-sipB (1222 bp): 1—VNP20009, 2—modified VNP20009; (B) product of cDNA amplification with primers specific for sipB (389 bp): 1—VNP20009, 2—modified VNP20009 and product of cDNA amplification for 16S rRNA (350 bp).

EXAMPLE 6

Removal of Antibiotic Resistance Gene from the VNP20009 Genome

Figure 9:
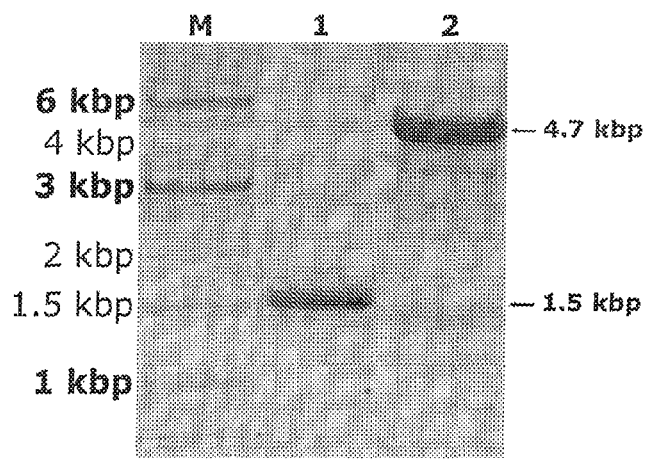

The above-mentioned genetic manipulations required the presence of an antibiotic resistance gene, which is undesirable in the final vaccine material. Therefore, this gene was deleted in the following stage. The cleavage of genomic DNA at the restriction site for I-SceI enzyme, which had been introduced into the genome together with the plasmid sequence, stimulated recombination with the participation of neighbouring regions of homology and selection of the clones, in which the DNA break was repaired. Clones with confirmed integration of the pSG76C-USS plasmid were subsequently transformed with plasmid pSTKST (with thermosensitive ori sequence pSC101) containing a gene for I-SceI meganuclease under the control of the tetracycline promoter. The clones were cultured on solid medium with kanamycin at 30° C. Then, individual colonies were transferred into liquid LB medium with kanamycin (20 µg/ml) and autoclaved chlortetracycline (cTc, 30 µg/ml, induces the expression of I-SceI by inactivating the tetracycline repressor) and incubated for 24 hours at 30° C. The culture was diluted 1:$10^6$, transferred to solid medium with kanamycin and cTc and cultured at 30° C. for 20 hours. Then, the clones were tested for the deletion of the resistance gene and for planned recombination with a PCR using pair of primers E and D—in this case the obtained product had 1526 by (FIG. 9, lane 1). PCR was performed using the primers A and D and a programme as follows: 94° C. 2 min, 94° C. 30 s, 58° C. 30 s, 70° C. 4 min, 10 cycles; 94° C. 30 s, 58° C. 30 s, 70° C. 4 min +10 sec/cycle, 20 cycles. The resulting product was longer than 4500 by and corresponded to the length of the ushA sequence with the integrated PsifB-sipB cassette (FIG. 9, path 2).

FIG. 9 shows the image of electrophoretic separation of the PCR product with primer sequences complementary to sequences flanking the ushA gene performed on the genomic DNA of a clone obtained with the procedure of PsifB-sipB integration into the VNP20009 chromosome. Amplification products were obtained with primers E and D (1526 bp) and with primers A and D (4709 bp).

Integration of the PsifB-sipB functional cassette into the VNP20009 chromosome is such a significant genetic modification of the bacteria, that it results in obtaining of a new bacterial strain.

EXAMPLE 7

Testing of the VNP/sipB (INT) Functionality

EXAMPLE 7A

Comparison of the Invasive Ability of VNP20009 And VNP/sipB Bacteria

The invasiveness VNP20009 and VNP/sipB strains was tested on RAW264.7 cells. No statistically significant differences in the invasiveness were found between "wild" and recombinant strains of VNP. RAW264.7 macrophage cell line was cultured on 48-well plates at the density of 2.5 ×104 in DMEM medium with 10% serum for 24 hours. The cells were infected with VNP20009 and VNP/sipB in 100 µl of OPTI-MEM® (reduced serum medium) (Invitrogen) without serum at MOI 5, determined by measuring optical density at 600 nm. After 1-hour of co-incubation of the cells with bacteria (37° C., 5% CO2), another 100 µl of OPTI-MEM® (reduced serum medium) (Invitrogen) supplemented serum and gentamicin (2% serum, 100µg/ml gentamicin) was added and incubated for 3 hours (37° C., 5% CO2) to eliminate extracellular bacteria. Then, the cells were harvested and transferred to LB/agar plates. The number of live intracellular bacteria was assessed based on the number of bacterial colonies present after 24-hour incubation and referred to the number of cells in the specific well.

Concurrently, the number of CFU per well of the start of infection was determined, based on the amount of bacterial colonies after 24-hour culturing on LB/agar plates, obtained from an appropriately diluted bacterial suspension used for the infection. Invasiveness of the bacteria was defined as the fraction of intracellular bacteria from the number of bacteria used for the infection (FIG. 10).

EXAMPLE 7B

Therapeutic Effects of VNP/sipB In A Mouse Tumour Model

Figure 11:

The experiment was performed on the CT26CEA lung metastasis model in Balb/c mice. Lungs were stained with Indian ink. FIG. 11 (upper row) shows lungs of the control mice isolated on day 15 after the intravenous administration of $5\times10^5$ CT26CEA cells. White spots visible on the dark background are small tumour foci and their number (>300 per lung) and randomly assessed volume illustrate the effectiveness of metastasis. The bottom row shows lungs taken from mice, which were administered *Salmonella typhimurium* VNP/sipB bacteria intranasally in the amount of $2\times10^7$ CFU/mouse 48 hours after the injection of cancer cells. In those lungs, an average of <20 tumours/lung were found. In the group of mice that were vaccinated with VNP/sipB, no detectable tumours were found in 50% of the examined lungs.

EXAMPLE 7C

Figure 12:
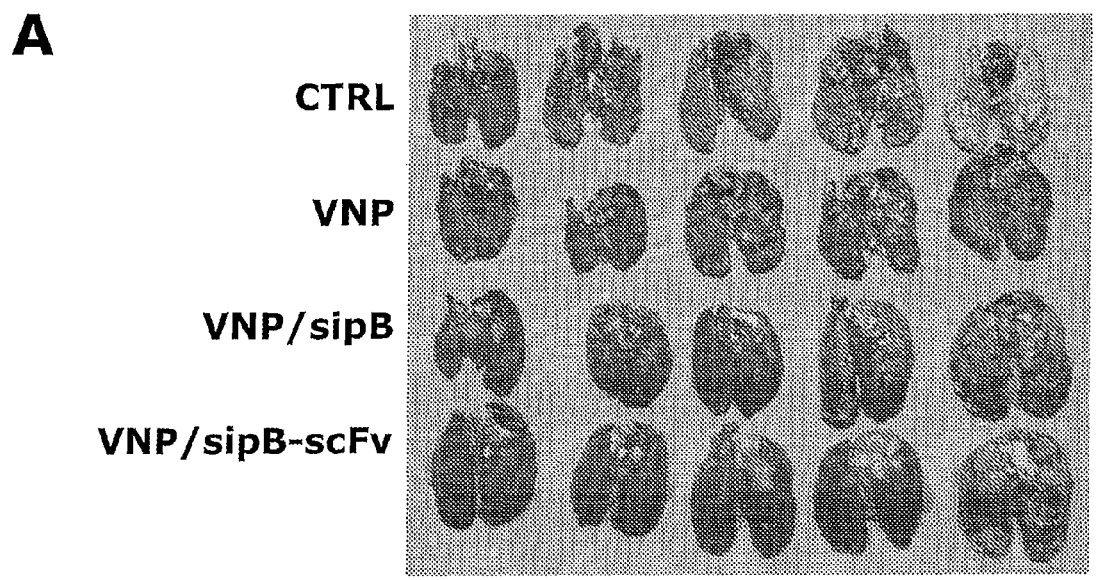
Figure 12:
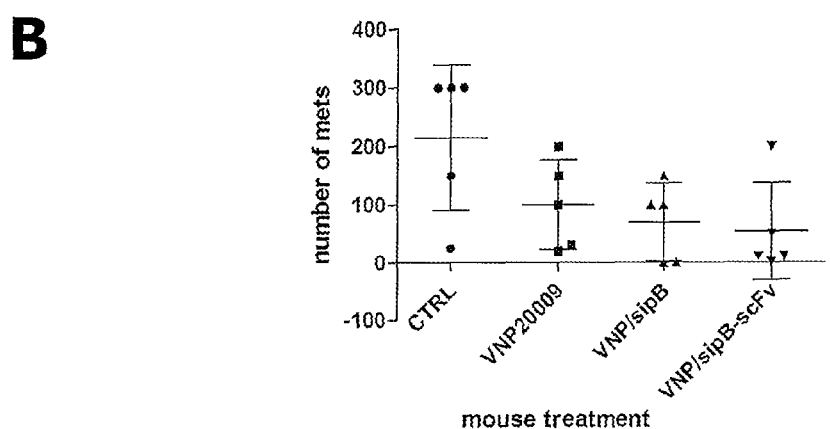

Comparison of Therapeutic Effects of Various VNP20009 Modifications In A Mouse Tumour Model The experiment was performed on the CT26CEA lung metastasis model in Balb/c mice. Lungs were stained with Indian ink. FIG. 12 (upper row) shows lungs of the control mice isolated on day 15 after intravenous administration of $5\times10^5$ CT26CEA cells. White spots visible on the dark background are small tumour foci and their number (>300 per lung) and randomly assessed volume illustrate the effectiveness of metastasis. The bottom row shows lungs taken from mice, which were administered various modifications of *Salmonella typhimurium* bacteria intranasally in the amount of $2\times10^7$ CFU/mouse 96 hours after the injection of cancer cells. In the lungs VNP/sipB vaccinated animals an average of 54 tumours/lung was found and 50% of the examined lungs did not have any detectable tumours; the mean numbers of tumour foci in the lungs are shown on the graph in the lower part of the figure.

EXAMPLE 7D

Figure 13:
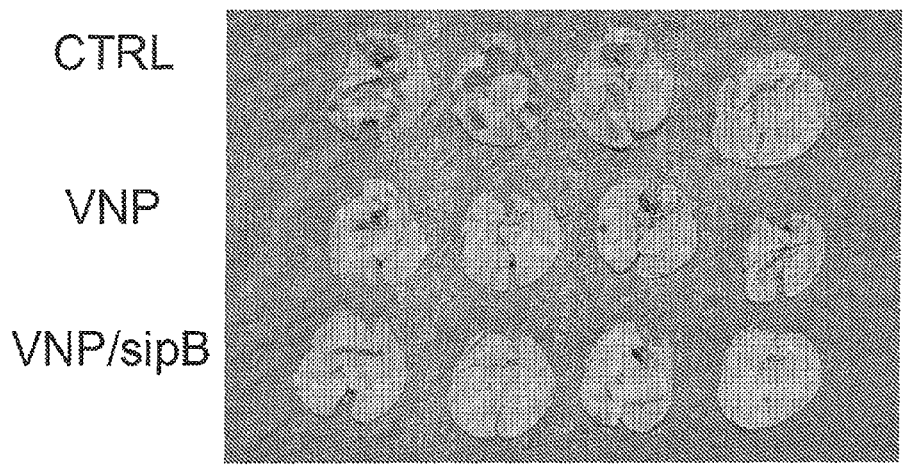

Comparison of Therapeutic Effects of VNP20009 And VNP/sipB In Mouse Tumour Model of B16F10 Melanoma The experiment was performed on the B16F10 lung metastasis model in C57Bl/6 mice (FIG. 13). Lungs were stained with picric acid. FIG. 13 (upper row) shows lungs of the control mice isolated on day 28 after intravenous administration of $5\times10^5$ B16F10 cells. Tumours are shown as dark dots and their number and randomly assessed size illustrate the effectiveness of metastasis. The middle and lower rows shows lungs isolated from mice, which were administered VNP (middle row) or VNP/sipB (bottom row) bacteria intranasally in the amount of $2\times10^7$ CFU/mouse 96 hours after the injection of cancer cells. In these lungs, less than 2 tumours/lung were found on average. In the group of mice that were vaccinated with VNP/sipB, no detectable tumours were found in 75% of the examined lungs.

EXAMPLE 7E

Selective Stimulation of Th1-Type Response By VNP/sipB

Figure 14:
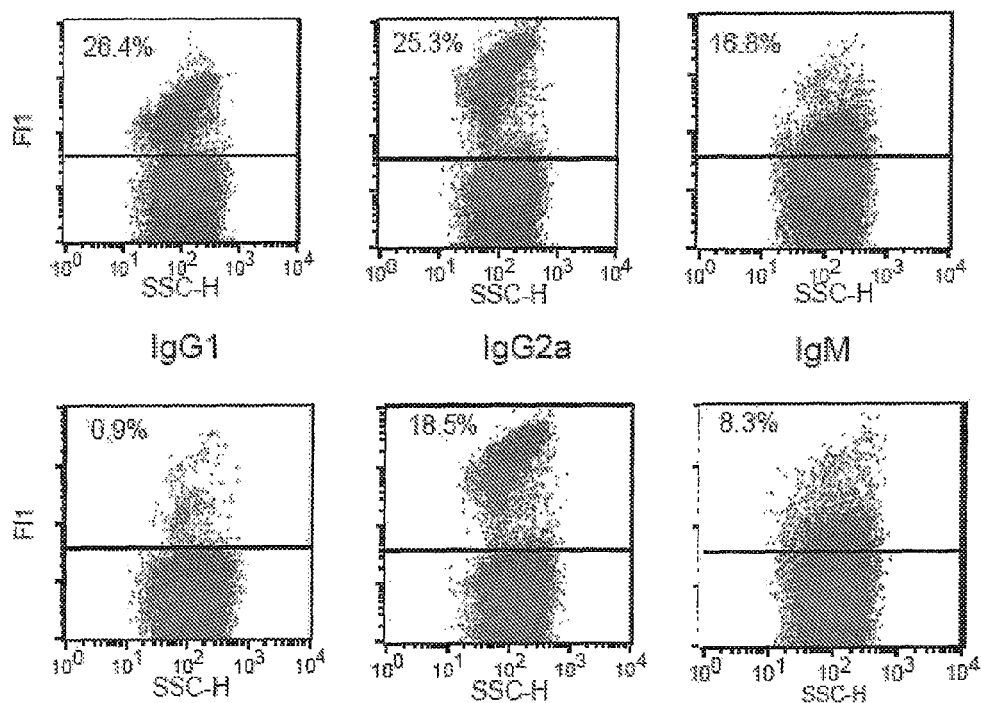

As an effect of the vaccination of Swiss mice (outbred) with the modified VNP20009 strains, immune response skewing towards a Th1-type response is found in half of the vaccinated animals (FIG. 14). While administration of the "wild type" VNP20009 (top panel) elicited all analysed antibody isotypes (IgG1, IgG2a and IgM), only high levels of IgG2a and the almost complete absence of IgG1 were found in the serum of mice vaccinated with VNP/sipB (bottom panel). It is very likely that the observed isotype skewing forms an important link in the chain of immune responses stimulated by VNP/sipB, which result, inter alia, in growth inhibition (or elimination) of tumours in the vaccinated mice.

EXAMPLE 7F

Apoptosis of VNP/sipB Infected MC38CEA Cells

Apoptosis induction in MC38CEA adenocarcinoma cells infected with VNP20009 or VNP/sipB was analyzed by flow cytometry of annexin V-stained cells. Bacteria transformed with the pDsRed2 plasmid encoding RFP (Red Fluorescent Protein) were used for the infection.

Cells were seeded on 24-well plate at 7.5·104 per well in DMEM containing 10% FBS and cultured at 37° C. in 5% CO2. Infection was carried out with bacteria suspended in 200 μl Opti-MEM at the multiplicity of infection equal to 20 bacteria per cell. Bacteria were allowed to invade cells for 45 min at 37° C. in 5% CO2. Then, 200 μl of gentamicin-containing Opti-MEM was added to kill extracellular bacteria (final concentration of gentamicin was 100 μg/ml). Incubation was continued for 1.5 h (37° C., 5% CO2). The media were then replaced with 0.5 ml Opti-MEM with 20 μg/ml gentamicin. After 20 h of incubation, cells were collected, stained with APC-labeled annexin V for 15 min at room temperature and analyzed by flow cytometry. FIG. 17 shows the percentage of annexin V binding cells gated on an RFP-positive, bacteria-infected population. There was around 10% more annexin V positive MC38CEA cells following infection with VNP/sipB than VNP20009.

EXAMPLE 8

Sequencing of the Recombinant Fragment of Genomic DNA of the Modified *Salmonella* enterica s. *Typhimurium* VNP20009 Strain The following DNA sequences were analysed: the ushA gene with its flanking sequences and the entire sequence of the integrated PsifB-sipB construct that in VNP/sipB bacteria is located within the ushA gene (FIG. 15A). The identity of the sequence from VNP/sipB with template DNA from a model strain of *Salmonella typhimurium*, LT2, was confirmed using BLAST software (NCBI). On the template (lower strand of DNA) in FIGS. 15B-15D, the location of the each element of the construct is indicated (sifB promoter, sipB ORF, ushA integration site) in accordance with the numbering of the LT2 strain deposited in GenBank (NCBI). Upper strand, marked as "Query", shows the sequence obtained from the VNP/sipB. The PsifB sequence in the genome of *Salmonella typhimurium* LT2 is located in the position 1 691 578-1 692 147 bp. The sipB sequence in the genome of *Salmonella typhimurium* LT2 is located in the position of 3

029 114-3 030 895 bp. The ushA sequence in the genome of *Salmonella typhimurium* LT2 is located in the position 553 634-555 286 bp.

Oligonucleotides used for sequencing of genomic DNA are listed in FIG. 16. The schematic location of the primers is indicated in FIG. 15 within the flanking sequences and the integrated construct.

As a result of the production of a properly modified strain of *Salmonella* enterica s. *Typhimurium*, a favourable therapeutic vaccine vector was produced, which is particularly suitable for use as an anti-cancer bacterial vaccine vector.

Deposited Materials

The stain of *Salmonella* enterica serovar *Typhimurium* VNP/sipB was deposited with the Polish Collection of Micro-orttanisms, Institute of Immunology and Experimental Therapy, Polish Academy of Sciences, Weigla 12, 53-114, Wroclaw, Poland, on Nov. 26, 2008, and has been assigned the indicated accession no. B/00024. The strain of *Salmonellal enterica* serovar *Typhimurium* VNP/sipB is a strain of *Salmonella enterica* serovar *Typhimurium* VNP20009 with a PsifB-sipB functional cassette integrated into its chromosome.

Literature
1. Hoiseth, S. K., and B. A. Stocker. 1981. Aromatic-dependent *Salmonella typhimurium* are non-virulent and effective as live vaccines. Nature 291:238-239.
2. Dougan, G., S. Chatfield, D. Pickard, J. Bester, D. O'Callaghan, and D. Maskell. 1988. Construction and characterization of vaccine strains of *Salmonella* harboring mutations in two different aro genes. J Infect Dis 158: 1329-1335.
3. Sydenham, M., G. Douce, F. Bowe, S. Ahmed, S. Chatfield, and G. Dougan. 2000. *Salmonella* enterica serovar *typhimurium* surA mutants are attenuated and effective live oral vaccines. Infect Immun 68:1109-1115.
4. Chatfield, S. N., K. Strahan, D. Pickard, I. G. Charles, C. E. Hormaeche, and G. Dougan. 1992. Evaluation of *Salmonella typhimurium* strains harbouring defined mutations in htrA and aroA in the murine salmonellosis model. Microb Pathog 12:145-151.
5. Coynault, C., V. Robbe-Saule, and F. Norel. 1996. Virulence and vaccine potential of *Salmonella typhimurium* mutants deficient in the expression of the RpoS (sigma S) regulon. Mol Microbiol 22:149-160.
6. Dougan, G., C. E. Hormaeche, and D. J. Maskell. 1987. Live oral *Salmonella* vaccines: potential use of attenuated strains as carriers of heterologous antigens to the immune system. Parasite Immunol 9:151-160.
7. Gentschev, I., S. Spreng, H. Sieber, J. Ures, F. Mollet, A. Collioud, J. Pearman, M. E. Griot-Wenk, J. Fensterle, U. R. Rapp, W. Goebel, S. A. Rothen, and G. Dietrich. 2007. Vivotif—a 'magic shield' for protection against typhoid fever and delivery of heterologous antigens. Chemotherapy 53:177-180.
8. Cheminay, C., and M. Hensel. 2008. Rational design of *Salmonella* recombinant vaccines. Int J Med Microbiol 298:87-98.
9. Bermudes, D., L. M. Zheng, and I. C. King. 2002. Live bacteria as anticancer agents and tumor-selective protein delivery vectors. Curr Opin Drug Discov Devel 5:194-199.
10. Pawelek, J. M., K. B. Low, and D. Bermudes. 1997. Tumor-targeted *Salmonella* as a novel anticancer vector. Cancer Res 57:4537-4544.
11. Clairmont, C., K. C. Lee, J. Pike, M. Ittensohn, K. B. Low, J. Pawelek, D. Bermudes, S. M. Brecher, D. Margitich, J. Turnier, Z. Li, X. Luo, I. King, and L. M. Zheng. 2000. Biodistribution and genetic stability of the novel antitumor agent VNP20009, a genetically modified strain of *Salmonella typhimurium*. J Infect Dis 181:1996-2002.
12. Toso, J. F., V. J. Gill, P. Hwu, F. M. Marincola, N. P. Restifo, D. J. Schwartzentruber, R. M. Sherry, S. L. Topalian, J. C. Yang, F. Stock, L. J. Freezer, K. E. Morton, C. Seipp, L. Haworth, S. Mavroukakis, D. White, S. MacDonald, J. Mao, M. Sznol, and S. A. Rosenberg. 2002. Phase I study of the intravenous administration of attenuated *Salmonella typhimurium* to patients with metastatic melanoma. J Clin Oncol 20:142-152.
13. Bereta, M., A. Hayhurst, M. Gajda, P. Chorobik, M. Targosz, J. Marcinkiewicz, and H. L. Kaufman. 2007. Improving tumor targeting and therapeutic potential of *Salmonella* VNP20009 by displaying cell surface CEA-specific antibodies. Vaccine 25:4183-4192.
14. Cossart, P., and P. J. Sansonetti. 2004. Bacterial invasion: the paradigms of enteroinvasive pathogens. Science 304: 242-248.
15. Hersh, D., D. M. Monack, M. R. Smith, N. Ghori, S. Falkow, and A. Zychlinsky. 1999. The *Salmonella* invasin SipB induces macrophage apoptosis by binding to caspase-1. Proc Natl Acad Sci USA 96:2396-2401.
16. Freeman, J. A., M. E. Ohl, and S. I. Miller. 2003. The *Salmonella* enterica serovar *typhimurium* translocated effectors SseJ and SifB are targeted to the *Salmonella*-containing vacuole. Infect Immun 71:418-427.
17. Posfai, G., V. Kolisnychenko, Z. Bereczki, and F. R. Blattner. 1999. Markerless gene replacement in *Escherichia coli* stimulated by a double-strand break in the chromosome. Nucleic Acids Res 27:4409-4415.
18. Burns, D. M., and I. R. Beacham. 1986. Identification and sequence analysis of a silent gene (ushAO) in *Salmonella typhimurium*. J Mol Biol 192:163-175.
19. Innes, D., I. R. Beacham, C. A. Beven, M. Douglas, M. W. Laird, J. C. Joly, and D. M. Burns. 2001. The cryptic ushA gene (ushA(c)) in natural isolates of *Salmonella* enterica (serotype *Typhimurium*) has been inactivated by a single missense mutation. Microbiology 147:1887-1896.

The invention claimed is:

1. A method of producing a vector, comprising introducing a nucleic acid containing a gene encoding sipB under the control of the PsifB promoter into *Salmonella* enterica serovar *Typhimurium* VNP20009.

2. The method of claim 1, wherein the nucleic acid is an expression cassette, and the expression cassette is integrated into the bacterial chromosome.

3. The method of claim 2, wherein the expression cassette is a PsifB-sipB cassette comprising SEQ ID NO 1 or a ushA-5'-PsifB-sipB-ushA-3' cassette comprising SEQ ID NO: 2.

4. The method of claim 2, the method further comprising removing it gene for antibiotic. resistance from *Salmonella* enterica serovar *Typhimurium* VNP20009.

5. The method of claim 1, wherein the vector is the strain of *Salmonella* enterica serovar *Typhimurium* VNP/sipB deposited at the Polish Collection of Microorganisms under the accession number B/00024.

* * * * *

UNITED STATES PATENT AND TRADEMARK OFFICE
CERTIFICATE OF CORRECTION

PATENT NO. : 8,916,372 B2  
APPLICATION NO. : 13/148139  
DATED : December 23, 2014  
INVENTOR(S) : Michal Bereta, Joanna Bereta and Paulina Chorobik Page 1 of 1

It is certified that error appears in the above-identified patent and that said Letters Patent is hereby corrected as shown below:

On the title page, column 1 (Assignee), line 1, delete "Crakow (PL)" and insert -- Kraków (PL) --;

In the Claims

In column 35, line 47, in Claim 3, delete "NO" and insert -- NO: --;

In column 36, line 40 (approx.), in Claim 4, delete "it" and insert -- a --;

In column 36, line 40 (approx.), in Claim 4, delete "antibiotic." and insert -- antibiotic --.

Signed and Sealed this  
Fourteenth Day of July, 2015

Michelle K. Lee  
*Director of the United States Patent and Trademark Office*

SEQUENCE LISTING

<160> NUMBER OF SEQ ID NOS: 33

<210> SEQ ID NO 1
<211> LENGTH: 2414
<212> TYPE: DNA
<213> ORGANISM: Artificial Sequence
<220> FEATURE:
<223> OTHER INFORMATION: Coding sequence of the PsifB-sipB cassette

<400> SEQUENCE: 1

```
ccttagccat tctgactgca aaatgcccca ggatgctgtc ttttcgtgaa tttcaccatc    60
tgatttcttc attttgagcc tcctcgcagg tttttataat tttatcgccc aactggaaac   120
aaagccgtca gctaatcgtt acaacaaata taattaagac aaaaactaaa gagtaagata   180
tttatatcat aagcactatc agtattggcc ttctgcccta ccgctaaaca tctcattgtt   240
gttagcctaa taatactttt agtttaactt cttataagac aatttctaca cggttgagca   300
actatttact ttctctaaaa ataatatagt gcgtaattaa tcattactca tagtacatga   360
tgatgtgaga attaagaaaa ccgttttact ttcattcgtt ttatctgaca tatttcatgg   420
ccaggaggcg tgggcatgac taaagctacg ggtcgatttg aacaattgaa caataatgtt   480
gacggttcag gacaaagcaa aaatcaggtg tttcaccgat aggcaaaccg atgggcaaca   540
tgggataata tttcgaatac cacctattcc agtaatgaag tgaagatctt ccagaggaga   600
aattaactat gagaggatcg catcaccatc accatcacgg atcccgaagt agcattagcc   660
gtagcggata tacccaaaat ccgcgcctcg ctgaggcggc ttttgaaggc gttcgtaaga   720
acacggactt tttaaaagcg gcggataaag cttttaaaga tgtggtggca acgaaagcgg   780
gcgaccttaa agccggaaca aagtccggcg agagcgctat taatacggtg ggtctaaagc   840
cgcctacgga cgccgcccgg gaaaaactct ccagcgaagg gcaattgaca ttactgcttg   900
gcaagttaat gaccctactg ggcgatgttt cgctgtctca actggagtct cgtctggcgg   960
tatggcaggc gatgattgag tcacaaaaag agatggggat tcaggtatcg aaagaattcc  1020
agacggctct gggagaggct caggaggcga cggatctcta tgaagccagt atcaaaaaga  1080
cggataccgc caagagtgtt tatgacgctg cgaccaaaaa actgacgcag gcgcaaaata  1140
aattgcaatc gctggacccg gctgaccccg gctatgcaca agctgaagcc gcggtagaac  1200
aggccggaaa agaagcgaca gaggcgaaag aggcttaga taaggccacg gatgcgacgg  1260
ttaaagcagg cacagacgcc aaagcgaaag ccgagaaagc ggataacatt ctgaccaaat  1320
tccagggaac ggctaatgcc gcctctcaga atcaggtttc ccagggtgag caggataatc  1380
tgtcaaatgt cgcccgcctc actatgctca tggccatgtt tattgagatt gtgggcaaaa  1440
atacggaaga aagcctgcaa aacgatcttg cgcttttcaa cgccttgcag gaagggcgtc  1500
aggcggagat ggaaaagaaa tcggctgaat tccaggaaga gacgcgcaaa gccgaggaaa  1560
cgaaccgcat tatgggatgt atcggaaag tcctcggcgc gctgctaacc attgtcagcg  1620
ttgtggccgc tgttttttacc ggtggggcga tctggcgct ggctgcggtg gacttgcgg  1680 taatggtggc cgatgaaatt gtgaaggcgg cgacgggagt gtcgtttatt cagcaggcgc  1740
taaacccgat tatggagcat gtgctgaagc cgttaatgga gctgattggc aaggcgatta  1800
ccaaagcgct ggaaggatta ggcgtcgata agaaaacggc agagatgccc ggcagcattg  1860
ttggtgcgat tgtcgccgct attgccatgg tggcggtcat tgtggtggtc gcagttgtcg  1920
ggaaaggcgc ggcggcgaaa ctgggtaacg cgctgagcaa aatgatgggc gaaacgatta  1980
agaagttggt gcctaacgtg ctgaaacagt tggcgcaaaa cggcagcaaa ctctttaccc  2040
aggggatgca acgtattact agcggtctgg gtaatgtggg tagcaagatg ggcctgcaaa  2100
cgaatgcctt aagtaaagag ctggtaggta ataccctaaa taaagtggcg ttgggcatgg  2160
aagtcacgaa taccgcagcc cagtcagccg gtggtgttgc cgagggcgta tttattaaaa  2220
atgccagcga ggcgcttgct gattttatgc tcgcccgttt tgccatggat cagattcagc  2280
agtggcttaa acaatccgta gaaatatttg gtgaaaacca gaaggtaacg gcggaactgc  2340
```

| | |
|---|---|
| aaaaagccat gtcttctgcg gtacagcaaa atgcggatgc ttcgcgtttt attctgcgcc | 2400 |
| agagtcgcgc ataa | 2414 |

<210> SEQ ID NO 2
<211> LENGTH: 4352
<212> TYPE: DNA
<213> ORGANISM: Artificial Sequence
<220> FEATURE:
<223> OTHER INFORMATION: Sequence of the ushA-5'-PsifB-sipB-ushA-3' construct

<400> SEQUENCE: 2

| | |
|---|---|
| gcgatgttgg agatagtagg atgtgtaatt attacttgcc taacatacct gtgaaatgtg | 60 |
| tttgaaggaa gtctcaattc tgaaaacata tttgtctatt attgcaagga aaggtaattt | 120 |
| ctgcggttga tattgagtca gggagagaaa gatgaaattt ttgaaacggg gtgtggcgct | 180 |
| ggcgttactg gcggcgttcg cgctgacgac tcagcctgca caggcttacg aaaaagataa | 240 |
| aacctataaa attactatcc tgcataccaa cgatcaccac ggtcacttct ggcgcagcga | 300 |
| atatggcgaa tatggtctgg cggcgcaaaa acgctggtg gacagtatcc gtaaagaggt | 360 |
| ggcgcaagag gggggaagcg tcctgttgtt atccggcggc gacattaata ccggggtgcc | 420 |
| ggaatccgat ctccaggatg cggagcccga tttccgcggg atgaatctga ttggctacga | 480 |
| cgctatggcc gtcggtaatc atgaatttga taatccgctc accgtattgc gccagcagga | 540 |
| aaagtgggcg aagtttccct ttctttacgc caatatttat caaaaaagta ccggcgagcg | 600 |
| tctgtttaag ccgtgggcta ttttacacg ccaggatata aaaatcgcgg taatcggctt | 660 |
| aaccaccgat gacacggcga aaataggcaa cccggaatat ttcaccgata ttgagtttcg | 720 |
| taaacctgct gaagaagcaa aggtggtgat tcaggaactt aatatgaatg aaaaaccgga | 780 |
| cgtgattatc gcgaccacgc atatgggaca ttatgacaac ggcgatcacg gttcgaacgc | 840 |
| gccgggcgac gttgagatgg cgcgtagcct gcctgccggt tcgttggcga tgattgtggg | 900 |
| cggtcactca caagacccgg tatgcatggc gtcgaaaat aaaaaacagg tgaattacgt | 960 |
| accgggaacg ccctgcgcgc cggataagca aaatggcatc tggatcgtgc aggcgcatga | 1020 |
| gtgggtaaa tatgtgggcc gtgcggattt cgaattccgt aacggcgaga tgaaaatggt | 1080 |
| tggccgcggg aattcgatga agatcttcgg agtccaagct cagctaatta agcttggctg | 1140 |
| cagaaccaat gcattggttt ctcccttat tttggcagtt tttatgcgcg actctggcgc | 1200 |
| agaataaaac gcgaagcatc gcattttgc tgtaccgcag aagacatggc tttttgcagt | 1260 |
| tccgccgtta ccttctggtt ttcaccaaat atttctacgg attgtttaag ccactgctga | 1320 |
| atctgatcca tggcaaaacg ggcgagcata aaatcagcaa gcgcctcgct ggcatttta | 1380 |
| ataaatacgc cctcggcaac accaccggct gactgggctg cggtattcgt gacttccatg | 1440 |
| cccaacgcca ctttatttag ggtattacct accagctctt tacttaaggc attcgtttgc | 1500 |
| aggcccatct tgctacccac attacccaga ccgctagtaa tacgttgcat ccctgggta | 1560 |
| aagagtttgc tgccgttttg cgccaactgt ttcagcacgt taggcaccaa cttcttaatc | 1620 |
| gtttcgccca tcattttgct cagcgcgtta cccagtttcg ccgccgcgcc tttcccgaca | 1680 |
| actgcgacca ccacaatgac cgccaccatg gcaatagcgg cgacaatcgc accaacaatg | 1740 |
| ctgccggcca tctctgccgt tttcttatcg acgcctaatc cttccagcgc tttggtaatc | 1800 |
| gccttgccaa tcagctccat taacggcttc agcacatgct ccataatcgg gtttagcgcc | 1860 |
| tgctgaataa acgacactcc cgtcgccgcc ttcacaattt catcggccac cattaccgca | 1920 |

```
agtcccaccg cagccagcgc cagactcgcc ccaccggtaa aaacagcggc cacaacgctg    1980
acaatggtta gcagcgcgcc gaggactttc ccgatacatc ccataatgcg gttcgtttcc    2040
tcggctttgc gcgtctcttc ctggaattca gccgatttct tttccatctc cgcctgacgc    2100
ccttcctgca aggcgttgaa aagcgcaaga tcgttttgca ggctttcttc cgtattttg     2160 cccacaatct caataaacat ggccatgagc atagtgaggc gggcgacatt tgacagatta    2220
tcctgctcac cctgggaaac ctgattctga gaggcggcat tagccgttcc ctggaatttg    2280
gtcagaatgt tatccgcttt tcggctttc gctttggcgt ctgtgcctgc tttaaccgtc     2340
gcatccgtgg ccttatctaa ggcctctttc gcctctgtcg cttcttttcc ggcctgttct    2400
accgcggctt cagcttgtgc atagccgggg tcagccgggt ccagcgattg caatttattt    2460
tgcgcctgcg tcagtttttt ggtcgcagcg tcataaacac tcttggcggt atccgtcttt    2520
ttgatactgg cttcatagag atccgtcgcc tcctgagcct ctcccagagc cgtctggaat    2580
tctttcgata cctgaatccc catctctttt tgtgactcaa tcatcgcctg ccataccgcc    2640
agacgagact ccagttgaga cagcgaaaca tcgcccagta gggtcattaa cttgccaagc    2700
agtaatgtca attgcccttc gctggagagt ttttcccggg cggcgtccgt aggcggcttt    2760
agacccaccg tattaatagc gctctcgccg gactttgttc cggctttaag gtcgcccgct    2820
ttcgttgcca ccacatcttt aaaagcttta tccgccgctt ttaaaaagtc cgtgttctta    2880
cgaacgcctt caaaagccgc ctcagcgagg gcgggatttt gggtatatcc gctacggcta    2940
atgctacttc gggatccgtg atggtgatgg tgatgcgatc ctctcatagt taatttctcc    3000 tctgaagat cttcacttca ttactggaat aggtggtatt cgaaatatta tcccatgttg     3060
cccatcggtt tgcctatcgg tgaaacacct gattttgct tgtcctgaa ccgtcaacat      3120 tattgttcaa ttgttcaaat cgaccgtag ctttagtcat gcccacgcct cctggccatg     3180
aaatatgtca gataaaacga atgaaagtaa acggttttc ttaattctca catcatcatg     3240
tactatgagt aatgattaat tacgcactat attatttta gagaaagtaa atagttgctc     3300
aaccgtgtag aaattgtctt ataagaagtt aaactaaaag tattattagg ctaacaacaa    3360
tgagatgttt agcggtaggg cagaaggcca atactgatag tgcttatgat ataaatatct    3420
tactctttag ttttttgtctt aattatattt gttgtaacga ttagctgacg gctttgtttc   3480
cagttgggcg ataaaattat aaaaacctgc gaggaggctc aaaatgaaga aatcagatgg    3540
tgaaattcac gaaaagacag catcctgggg cattttgcag tcagaatggc taaggcccaa    3600
gcttgggaat cactagtgaa ttcgcggcca actaccagct tattccggta atctcaaga    3660 aaaaagtgac ctgggataac gggaaaagcg agcgtgtact ttacacgccg gaaatcgcag    3720
aaaatccgca aatgctctcg ttattaacgc cgttccagaa taaaggtaaa gcgcaactgg    3780
aggtgaaaat tggtagcgtg aatggccttc ttgaaggcga tcgcagtaag gtcagatttg    3840
tccagaccaa tatgggacgg gtgattctgg ctgcgcagat cgcgcgcacc ggcgccgatt    3900
ttggcgtgat gagcggcggc ggtattcgcg actcgattga ggcgggagat attacctata    3960
aaagcgtgct caaggtacag ccgttcggca acattgtggt gtatgccgat atgagcggca    4020
aagaggtggt tgattatctc accgccgtag cacagatgaa accggactcc ggcgcctatc    4080
cacagctcgc caatgtgagc tttgtcgcca agagggcaa gctcaccgat ctgaaaatca    4140
aaggcgagcc tgttgatccg gctaaaacct atcgcatggc gacgctgagt ttcaacgcca    4200
cgggcggcga tggttatccg cgcattgata caaaccggg ctacgtgaat accgggttta    4260
ttgacgcgga agtgctgaaa gagtttattc agcaaaattc accgctggat gcggcggcgt    4320
```

-continued

```
ttacgccaaa tggtgaggtg agctggctgt ag                                    4352

<210> SEQ ID NO 3
<211> LENGTH: 42
<212> TYPE: DNA
<213> ORGANISM: Artificial Sequence
<220> FEATURE:
<223> OTHER INFORMATION: SipB gene primer

<400> SEQUENCE: 3
aactgcagaa ccaatgcatt ggtttctccc tttattttgg ca                         42

<210> SEQ ID NO 4
<211> LENGTH: 30
<212> TYPE: DNA
<213> ORGANISM: Artificial Sequence
<220> FEATURE:
<223> OTHER INFORMATION: SipB gene primer reverse

<400> SEQUENCE: 4
gcgatgccga ttacgatgaa gccctagggc                                       30

<210> SEQ ID NO 5
<211> LENGTH: 30
<212> TYPE: DNA
<213> ORGANISM: Artificial Sequence
<220> FEATURE:
<223> OTHER INFORMATION: sifB gene primer forward

<400> SEQUENCE: 5
cccaagcttg ggccttagcc attctgactg                                       30

<210> SEQ ID NO 6
<211> LENGTH: 33
<212> TYPE: DNA
<213> ORGANISM: Artificial Sequence
<220> FEATURE:
<223> OTHER INFORMATION: sifB gene primer reverse

<400> SEQUENCE: 6
gaagatcttc acttcattac tggaataggt ggt                                   33

<210> SEQ ID NO 7
<211> LENGTH: 32
<212> TYPE: DNA
<213> ORGANISM: Artificial Sequence
<220> FEATURE:
<223> OTHER INFORMATION: GFP primer forward

<400> SEQUENCE: 7
gaagatcttc tcacacagga aacagctatg ac                                    32

<210> SEQ ID NO 8
<211> LENGTH: 28
<212> TYPE: DNA
<213> ORGANISM: Artificial Sequence
<220> FEATURE:
<223> OTHER INFORMATION: GFP primer reverse

<400> SEQUENCE: 8
gaagatcttc gcgctcagtt ggaattca                                         28

<210> SEQ ID NO 9
<211> LENGTH: 34
<212> TYPE: DNA
```

```
<213> ORGANISM: Artificial Sequence
<220> FEATURE:
<223> OTHER INFORMATION: sipB primer forward

<400> SEQUENCE: 9
ggaagatctt ccagaggaga aattaactat gaga                              34

<210> SEQ ID NO 10
<211> LENGTH: 28
<212> TYPE: DNA
<213> ORGANISM: Artificial Sequence
<220> FEATURE:
<223> OTHER INFORMATION: sipB primer reverse

<400> SEQUENCE: 10
gaagatcttc ggagtccaag ctcagcta                                     28

<210> SEQ ID NO 11
<211> LENGTH: 30
<212> TYPE: DNA
<213> ORGANISM: Artificial Sequence
<220> FEATURE:
<223> OTHER INFORMATION: primer forward FushA

<400> SEQUENCE: 11
ggggtacccc gcgatgttgg agatagtagg                                   30

<210> SEQ ID NO 12
<211> LENGTH: 28
<212> TYPE: DNA
<213> ORGANISM: Artificial Sequence
<220> FEATURE:
<223> OTHER INFORMATION: primer reverse RushA

<400> SEQUENCE: 12
ggggtacccc tacagccagc tcacctca                                     28

<210> SEQ ID NO 13
<211> LENGTH: 30
<212> TYPE: DNA
<213> ORGANISM: Artificial Sequence
<220> FEATURE:
<223> OTHER INFORMATION: primer FushA

<400> SEQUENCE: 13
ggggtacccc gcgatgttgg agatagtagg                                   30

<210> SEQ ID NO 14
<211> LENGTH: 28
<212> TYPE: DNA
<213> ORGANISM: Artificial Sequence
<220> FEATURE:
<223> OTHER INFORMATION: primer RushA

<400> SEQUENCE: 14
ggggtacccc tacagccagc tcacctca                                     28

<210> SEQ ID NO 15
<211> LENGTH: 18
<212> TYPE: DNA
<213> ORGANISM: Artificial Sequence
<220> FEATURE:
<223> OTHER INFORMATION: primer A

<400> SEQUENCE: 15
gcgactggat catatcgt                                                18
```

<210> SEQ ID NO 16
<211> LENGTH: 18
<212> TYPE: DNA
<213> ORGANISM: Artificial Sequence
<220> FEATURE:
<223> OTHER INFORMATION: primer B

<400> SEQUENCE: 16
cgcctcacta tgctcatg                                            18

<210> SEQ ID NO 17
<211> LENGTH: 20
<212> TYPE: DNA
<213> ORGANISM: Artificial Sequence
<220> FEATURE:
<223> OTHER INFORMATION: primer C

<400> SEQUENCE: 17
ctgaacggtc tggttatagg                                          20

<210> SEQ ID NO 18
<211> LENGTH: 18
<212> TYPE: DNA
<213> ORGANISM: Artificial Sequence
<220> FEATURE:
<223> OTHER INFORMATION: primer D

<400> SEQUENCE: 18
ctggatattg aactggcg                                            18

<210> SEQ ID NO 19
<211> LENGTH: 30
<212> TYPE: DNA
<213> ORGANISM: Artificial Sequence
<220> FEATURE:
<223> OTHER INFORMATION: primer E

<400> SEQUENCE: 19
cccaagcttg ggccttagcc attctgactg                               30

<210> SEQ ID NO 20
<211> LENGTH: 20
<212> TYPE: DNA
<213> ORGANISM: Artificial Sequence
<220> FEATURE:
<223> OTHER INFORMATION: primer F

<400> SEQUENCE: 20
gcaggtcgac tctagaggat                                          20

<210> SEQ ID NO 21
<211> LENGTH: 30
<212> TYPE: DNA
<213> ORGANISM: Artificial Sequence
<220> FEATURE:
<223> OTHER INFORMATION: primer G

<400> SEQUENCE: 21
cccaagcttg ggccttagcc attctgactg                               30

<210> SEQ ID NO 22
<211> LENGTH: 563
<212> TYPE: DNA
<213> ORGANISM: Salmonella typhimurium VPN2009

<400> SEQUENCE: 22

```
aatgcccagg atgctgtctt ttcgtggatt tcaccatctg atttcttcat tttgagcctc    60
ctcgcaggtt tttataattt tatcgcccaa ctggaaacaa agccgtcagc taatcgttac   120
aacaaatata attaagacaa aaactaaaga gtaagatatt tatatcataa gcactatcag   180
tattggcctt ctgccctacc gctaaacatc tcattgttgt tagcctaata atacttttag   240
tttaacttct tataagacaa tttctacacg gttgagcaac tatttacttt ctctaaaaat   300
aatatagtgc gtaattaatc attactcata gtacatgatg atgtgagaat taagaaaacc   360
gttttacttt cattcgtttt atctgacata tttcatggcc aggaggcgtg ggcatgacta   420
aagctacggg tcgatttgaa caattgaaca ataatgttga cggttcagga caaagcaaaa   480
atcagggggt tcccccgata ggcaaaccga tggggcaaca tgggataata tttccgaata   540
ccaccctatt cccaggtaat gaa                                           563
```

<210> SEQ ID NO 23
<211> LENGTH: 558
<212> TYPE: DNA
<213> ORGANISM: Salmonella typhimurium LT2

<400> SEQUENCE: 23

```
aatgccccag gatgctgtct tttcgtgaat ttcaccatct gatttcttca ttttgagcct    60
cctcgcaggt ttttataatt ttatcgccca actggaaaca aagccgtcag ctaatcgtta   120
caacaaatat aattaagaca aaaactaaag agtaagatat ttatatcata agcactatca   180
gtattggcct tctgccctac cgctaaacat ctcattgttg ttagcctaat aatactttta   240
gtttaacttc ttataagaca atttctacac ggttgagcaa ctatttactt tctctaaaaa   300
taatatagtg cgtaattaat cattactcat agtacatgat gatgtgagaa ttaagaaaac   360
cgttttactt tcattcgttt tatctgacat atttcatggc caggaggcgt gggcatgact   420
aaagctacgg gtcgatttga acaattgaac aataatgttg acggttcagg acaaagcaaa   480
aatcaggtgt ttcaccgata ggcaaaccga tgggcaacat gggataatat ttcgaatacc   540
acctattcca gtaatgaa                                                 558
```

<210> SEQ ID NO 24
<211> LENGTH: 521
<212> TYPE: DNA
<213> ORGANISM: Salmonella typhimurium VPN2009

<400> SEQUENCE: 24

```
ccagtagggt cttacttgcc agcagtaatg tcaattgccc ttcgctggag agttttccc     60
gggcggcgtc cgtaggcggc tttagaccca ccgtattaat agcgctctcg ccggactttg   120
ttccggcttt aaggtcgccc gctttcgttg ccaccacatc tttaaaagct ttatccgccg   180
cttttaaaaa gtccgtgttc ttacgaacgc cttcaaaagc cgcctcagcg aggcgcggat   240
tttgggtata tccgctacgg ctaatgctac ttacttcatt actggaaata ggtggtattc   300
gaatattatc ccatgttgcc catcggtttg cctatcggtg aaacacctga ttttttgcttg   360
tcctgaaccg tcaacattat tgttcaattg ttcaatccga cccgtagctt tagtcatggc   420
ccccctcct gggccatgaa atatgtccga ataaaacgaa tggaagtaaa acgggttttc    480
ttaattcccc aatccatccg ggaccattga gtaaggatta a                       521
```

<210> SEQ ID NO 25
<211> LENGTH: 520

<212> TYPE: DNA
<213> ORGANISM: Salmonella typhimurium LT2

<400> SEQUENCE: 25

```
ccagtagggt cattaacttg ccaagcagta atgtcaattg cccttcgctg gagagttttt      60
cccgggcggc gtccgtaggc ggctttagac ccaccgtatt aatagcgctc tcgccggact     120
ttgttccggc tttaaggtcg cccgctttcg ttgccaccac atctttaaaa gctttatccg     180
ccgcttttaa aaagtccgtg ttcttacgaa cgccttcaaa agccgcctca gcgaggcgcg     240
gattttgggt atatccgcta cggctaatgc tacttacttc attactggaa taggtggtat     300
tcgaaatatt atcccatgtt gcccatcggt ttgcctatcg gtgaaacacc tgattttgc      360
tttgtcctga accgtcaaca ttattgttca attgttcaaa tcgacccgta gctttagtca     420
tgcccacgcc tcctggccat gaaatatgtc agataaaacg aatgaaagta aaacggtttt     480
cttaattctc acatcatcat gtactatgag taatgattaa                           520
```

<210> SEQ ID NO 26
<211> LENGTH: 686
<212> TYPE: DNA
<213> ORGANISM: Salmonella typhimurium VPN2009
<220> FEATURE:
<221> NAME/KEY: misc_feature
<222> LOCATION: 586, 602, 605, 610, 614, 622, 641, 643, 644, 655, 658,
    662, 666, 667, 669
<223> OTHER INFORMATION: n = A,T,C or G

<400> SEQUENCE: 26

```
aagtagcatt agccgtcccg gatatacccca aaatccgcgc ctcgctgagg cggcttttga      60
aggcgttcgt aagaacacgg acttttttaaa agcggcggat aaagctttta aagatgtggt     120
ggcaacgaaa gcgggcgacc ttaaagccgg aacaaagtcc ggcgagagcg ctattaatac     180
ggtgggtcta aagccgccta cggacgccgc ccgggaaaaa ctctccagcg aagggcaatt     240
gacattactg cttggcaagt taatgaccct actgggcgat gtttcgctgt ctcaactgga     300
gtctcgtctg gcggtatggc aggcgatgat tgagtcacaa aaagagatgg ggattcaggt     360
atcgaaagaa ttccagacgg ctctgggaga ggctcaggag gcgacggatc tctatgaagc     420
cagtatcaaa aagacggata ccgccaagag tgtttatgac gctgcgacca aaaaaactga     480
cgcaggcgca aaataaattg caatcgctgg gacccgggct gaccccggct atgcccaagc     540
tgaaacccac ggtaaaacca gggccggaaa agaaacgacc agaggncgaa agaggccttt     600
anaanaaggn cccnggaagg cnaccggggtt aaagccaggc ncnnaacccc caaangcnaa     660
angccnnana aaggcggaat aacatt                                          686
```

<210> SEQ ID NO 27
<211> LENGTH: 664
<212> TYPE: DNA
<213> ORGANISM: Salmonella typhimurium LT2

<400> SEQUENCE: 27

```
aagtagcatt agccgtagcg gatatacccca aaatccgcgc ctcgctgagg cggcttttga      60
aggcgttcgt aagaacacgg acttttttaaa agcggcggat aaagctttta aagatgtggt     120
ggcaacgaaa gcgggcgacc ttaaagccgg aacaaagtcc ggcgagagcg ctattaatac     180
ggtgggtcta aagccgccta cggacgccgc ccgggaaaaa ctctccagcg aagggcaatt     240
gacattactg cttggcaagt taatgaccct actgggcgat gtttcgctgt ctcaactgga     300
gtctcgtctg gcggtatggc aggcgatgat tgagtcacaa aaagagatgg ggattcaggt     360
```

```
atcgaaagaa ttccagacgg ctctgggaga ggctcaggag gcgacggatc tctatgaagc      420
cagtatcaaa aagacggata ccgccaagag tgtttatgac gctgcgacca aaaaactgac      480
gcaggcgcaa aataaattgc aatcgctgga cccggctgac cccggctatg cacaagctga      540
agccgcggta gaacaggccg gaaaagaagc gacagaggcg aaagaggcct tagataaggc      600
cacggatgcg acggttaaag caggcacaga cgccaaagcg aaagccgaga agcggataa       660 catt                                                                  664
```

<210> SEQ ID NO 28
<211> LENGTH: 562
<212> TYPE: DNA
<213> ORGANISM: Salmonella typhimurium VPN2009
<220> FEATURE:
<221> NAME/KEY: misc_feature
<222> LOCATION: 547
<223> OTHER INFORMATION: n = A,T,C or G

<400> SEQUENCE: 28

```
tgtgggccgt gcggatttcg aattccgtaa cggcgagatg aaatggtttt tctccctttta     60 ttttggcagt ttttatgcgc gactctggcg cagaataaaa cgcgaagcat ccgcattttg     120
ctgtaccgca gaagacatgg cttttgcag ttccgccgtt accttctggt tttcaccaaa      180
tatttctacg gattgtttaa gccactgctg aatctgatcc atggcaaaac gggcgagcat     240
aaaatcagca agcgcctcgc tggcattttt aataaatacg cccctcggca acaccaccgg     300
ctgactgggg ctgcggtatt cgtgacttcc atgcccaacg ccactttatt tagggtatta     360
cctaccagct ctttacttaa ggcattcgtt tgcaggccca tcttgctacc cacattaccc     420
agaccgctag taatacgttg catcccctg gggtaaaaaa gttggctgcc gttttgcgcc      480
aactgtttca gccacgttag gcaccaaact ccttaatccg tttcgcccat caattttggc     540
tcaagcnggg ttaccccagt tt                                              562
```

<210> SEQ ID NO 29
<211> LENGTH: 550
<212> TYPE: DNA
<213> ORGANISM: Salmonella typhimurium LT2

<400> SEQUENCE: 29

```
tgtgggccgt gcggatttcg aattccgtaa cggcgagatg aaaatggttt ttctcccttt      60
attttggcag ttttatgcg cgactctggc gcagaataaa acgcgaagca tccgcatttt      120
gctgtaccgc agaagacatg gcttttgca gttccgccgt taccttctgg ttttcaccaa      180
atatttctac ggattgttta agccactgct gaatctgatc catggcaaaa cgggcgagca     240
taaaatcagc aagcgcctcg ctggcatttt taataaatac gccctcggca acaccaccgg     300
ctgactgggc tgcggtattc gtgacttcca tgcccaacgc actttattt agggtattac      360 ctaccagctc tttacttaag gcattcgttt gcaggccat cttgctaccc acattaccca       420
gaccgctagt aatacgttgc atcccctggg taaagagttt gctgccgttt tgcgccaact     480
gtttcagcac gttaggcacc aacttcttaa tcgtttcgcc catcattttg ctcagcgcgt     540
tacccagttt                                                            550
```

<210> SEQ ID NO 30
<211> LENGTH: 18
<212> TYPE: DNA
<213> ORGANISM: Artificial Sequence
<220> FEATURE:

```
<223> OTHER INFORMATION: A Fusha1 primer

<400> SEQUENCE: 30
aatggcatct ggatcgtg                                                    18

<210> SEQ ID NO 31
<211> LENGTH: 18
<212> TYPE: DNA
<213> ORGANISM: Artificial Sequence
<220> FEATURE:
<223> OTHER INFORMATION: B Sipseq3 primer

<400> SEQUENCE: 31
gtaatcgcct tgccaatc                                                    18

<210> SEQ ID NO 32
<211> LENGTH: 20
<212> TYPE: DNA
<213> ORGANISM: Artificial Sequence
<220> FEATURE:
<223> OTHER INFORMATION: C sipseq4 primer

<400> SEQUENCE: 32
agacgagact ccagttgaga                                                  20

<210> SEQ ID NO 33
<211> LENGTH: 18
<212> TYPE: DNA
<213> ORGANISM: Artificial Sequence
<220> FEATURE:
<223> OTHER INFORMATION: F sipseq1 primer

<400> SEQUENCE: 33
gaggcgacgg atctctat                                                    18
```